United States Patent
Lowery et al.

(10) Patent No.: US 11,969,411 B2
(45) Date of Patent: *Apr. 30, 2024

(54) ADMINISTRATION OF BERBERINE METABOLITES

(71) Applicant: AXCESS GLOBAL SCIENCES, LLC, Salt Lake City, UT (US)

(72) Inventors: Ryan Lowery, Tampa, FL (US); Jacob Wilson, Tampa, FL (US); Terry LaCore, Melissa, TX (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/341,312

(22) Filed: Jun. 7, 2021

(65) Prior Publication Data

US 2022/0047578 A1 Feb. 17, 2022

Related U.S. Application Data

(63) Continuation of application No. 16/403,992, filed on May 6, 2019, now Pat. No. 11,026,929, which is a continuation-in-part of application No. 15/491,933, filed on Apr. 19, 2017, now Pat. No. 10,278,961.

(60) Provisional application No. 62/324,794, filed on Apr. 19, 2016.

(51) Int. Cl.
| | | |
|---|---|---|
| A61K 31/4355 | (2006.01) | |
| A61K 9/107 | (2006.01) | |
| A61K 31/00 | (2006.01) | |
| A61K 31/19 | (2006.01) | |
| A61K 31/4745 | (2006.01) | |
| A61K 36/889 | (2006.01) | |
| A61K 45/06 | (2006.01) | |
| A61K 47/44 | (2017.01) | |
| A61K 47/69 | (2017.01) | |
| A61P 3/08 | (2006.01) | |
| A61K 9/00 | (2006.01) | |

(52) U.S. Cl.
CPC ........ *A61K 31/4355* (2013.01); *A61K 9/1075* (2013.01); *A61K 31/00* (2013.01); *A61K 31/19* (2013.01); *A61K 31/4745* (2013.01); *A61K 36/889* (2013.01); *A61K 45/06* (2013.01); *A61K 47/44* (2013.01); *A61K 47/6911* (2017.08); *A61P 3/08* (2018.01); *A61K 9/0053* (2013.01)

(58) Field of Classification Search
CPC .................................................. A61K 47/6911
See application file for complete search history.

(56) References Cited

U.S. PATENT DOCUMENTS

| | | | |
|---|---|---|---|
| 6,031,000 A | 2/2000 | Nissen et al. | |
| 6,207,856 B1 | 3/2001 | Veech | |
| 6,380,244 B2 | 4/2002 | Martin et al. | |
| 7,807,718 B2 | 10/2010 | Hashim et al. | |
| 8,071,641 B2 | 12/2011 | Weiss et al. | |
| 8,642,654 B2 | 2/2014 | Clarke et al. | |
| 10,245,242 B1 | 4/2019 | Millet | |
| 10,245,243 B1 | 4/2019 | Millet | |
| 10,278,961 B2 * | 5/2019 | Lowery | ................ A61K 38/005 |
| 11,026,929 B2 * | 6/2021 | Lowery | .............. A61K 47/6911 |
| 2002/0013339 A1 | 1/2002 | Martin et al. | |
| 2002/0124370 A1 | 9/2002 | Deckert et al. | |
| 2009/0306221 A1 | 12/2009 | Guy et al. | |
| 2010/0113494 A1 | 5/2010 | Hu et al. | |
| 2014/0350105 A1 | 11/2014 | D'Agostino et al. | |
| 2015/0063140 A1 | 3/2015 | Yi et al. | |
| 2015/0065571 A1 | 3/2015 | Clarke et al. | |
| 2016/0272603 A1 | 9/2016 | Kravchenko et al. | |
| 2017/0296501 A1 | 10/2017 | Lowery et al. | |
| 2017/0296520 A1 | 10/2017 | Lowery et al. | |
| 2018/0020699 A1 | 1/2018 | Steup | |
| 2019/0313682 A1 | 10/2019 | Nagel | |
| 2020/0061004 A1 | 2/2020 | Millet | |
| 2020/0129463 A1 | 4/2020 | Lowery et al. | |
| 2022/0133673 A1 | 5/2022 | Millet | |
| 2022/0202760 A1 | 6/2022 | Greenwood et al. | |

FOREIGN PATENT DOCUMENTS

| | | |
|---|---|---|
| CN | 1104978 C | 4/2003 |
| CN | 1184978 C | 1/2005 |
| EP | 1755743 B1 | 4/2013 |
| JP | 5690261 B2 | 3/2015 |

(Continued)

OTHER PUBLICATIONS

Allendorfer et al., "Neuroimaging studies towards understanding the central effects of pharmacological cannabis products on patients with epilepsy", Epilepsy Behav, May 2017, vol. 70, pp. 349-354.
EnergyTimes—Herbal keto support Jan. 15, 2008.
European Search Report received for EP Patent Application No. 19880284.5, dated Jul. 12, 2022, 11 pages.
International Preliminary Report on Patentability received for PCT Patent Application No. PCT/US17/28465, dated Nov. 1, 2018, 7 pages.
International Preliminary Report on Patentability received for PCT Patent Application No. PCT/US17/28466, dated Nov. 1, 2018, 8 pages.

(Continued)

*Primary Examiner* — Paul V Ward
(74) *Attorney, Agent, or Firm* — Workman Nydegger

(57) ABSTRACT

In various implementations, berberine metabolites, such as dihydroberberine and/or tetrahydroberberine, may be administered to manage blood glucose levels, increase ketone levels (e.g., blood concentration of ketones), and/or for therapeutic purposes in humans. The administration of a pharmaceutically effective amount of berberine metabolites, such as dihydroberberine, may reduce fasting blood glucose levels, improve glucose tolerance, and/or improve blood ketone response. In some implementations, berberine metabolites may be administered with one or more other compounds.

20 Claims, 16 Drawing Sheets

(56) References Cited

FOREIGN PATENT DOCUMENTS

| | | |
|---|---|---|
| WO | 00/04895 A2 | 2/2000 |
| WO | 00/15216 A1 | 3/2000 |
| WO | 2005/077348 A1 | 8/2005 |
| WO | 2006/029577 A1 | 3/2006 |
| WO | 2007/138322 A1 | 12/2007 |
| WO | 2008/021394 A2 | 2/2008 |
| WO | 2010/021766 A1 | 2/2010 |
| WO | 2010/104595 A1 | 9/2010 |
| WO | 2012/024611 A1 | 2/2012 |
| WO | 2014/153415 A2 | 9/2014 |
| WO | 2014/153416 A1 | 9/2014 |
| WO | 2015/063140 A1 | 5/2015 |
| WO | 2017/156446 A1 | 9/2017 |
| WO | 2017/184788 A1 | 10/2017 |
| WO | 2018/132189 A1 | 7/2018 |
| WO | 2019/200132 A1 | 10/2019 |
| WO | 2020/092451 A1 | 5/2020 |
| WO | 2022/040644 A2 | 2/2022 |

OTHER PUBLICATIONS

International Preliminary Report on Patentability received for PCT Patent Application No. PCT/US19/58676, dated May 14, 2021, 6 pages.
International Search Report and Written Opinion received for PCT Patent Application No. PCT/US17/28466, dated Jul. 5, 2017, 8 pages.
International Search Report and Written Opinion received for PCT Patent Application No. PCT/US19/58676, dated Jan. 16, 2020, 6 pages.
International Search Report and Written Opinion received for PCT Patent Application No. PCT/US2023/020407, dated Jul. 26, 2023, 10 pages.
International Search Report and Written Opinion received for PCT Patent Application No. PCT/US2023/020417, dated Jul. 21, 2023, 11 pages.
International Search Report and Written Opinion received for PCT Patent Application No. PCT/US22/36030, dated Oct. 7, 2022, 7 pages.
International Search Report and Written Opinion received for PCT Patent Application No. PCT/US17/28465, dated Jul. 5, 2017, 7 pages.
Lannotti et al., "Effects of non-euphoric plant cannabinoids on muscle quality and performance of dystrophic mdx mice", Br J Pharmacol, May 2019, vol. 176, No. 10, pp. 1568-1584.
Office Action received for European Patent Application No. 17786592.0, dated Jun. 17, 2022, 7 pages.
Office Action received for European Patent Application No. 17786592.0, dated Sep. 25, 2020, 7 pages.
Stefan et al., "The Effects of Exogenous Beta-Hydroxybutyrate Supplementation on Metrics of Safety and Health", International Journal of Nutrition and Food Sciences, vol. 9, No. 6, Nov. 2020, pp. 154-162.
Supplementary European Search Report received for EP Patent Application No. 17786592.0, dated Nov. 25, 2019, 10 pages.
Decision to grant received for European Patent Application No. 17786592.0, mailed on Nov. 3, 2023, 2 pages.
Dedkova et al. "Role of B-hydroxybutyrate, its polymer poly-b-hydroxybutyrate and inorganic polyphosphate in mammalian health and disease", Frontiers in Physiology, Jul. 17, 2014, pp. 1-22.
Newman et al. "B-Hydroxybutyrate: A Signaling Metabolite", Annu Rev Nutr., Aug. 21, 2017, pp. 1-30.
Newman et al., "B-hydroxybutyrate: Much more than a metabolite", Diabetes Res Clin Pract., Nov. 2014.
Office Action received for European Patent Application No. 19880284.5, mailed on Nov. 9, 2023, 5 pages.

\* cited by examiner

| Subject 1 | | Subject 2 | | Subject 3 | | Subject 4 | | Subject 5 | |
|---|---|---|---|---|---|---|---|---|---|
| 1 | 500 mg DHBB | 1 | 250 mg DHBB | 1 | 250 mg DHBB | 1 | 500 mg DHBB | 1 | 500 mg DHBB |
| 2 | 250 mg DHBB | 2 | 500 mg DHBB | 2 | 500 mg DHBB | 2 | 250 mg DHBB | 2 | 500 mg BB HCL |
| 3 | 500 mg BB HCL | 3 | 500 mg BB HCL | 3 | 500 mg BB HCL | 3 | 500 mg BB HCL | 3 | 250 mg DHBB |

| Subject | Condition | Baseline | 30 minutes | 60 minutes | 90 minutes | 120 minutes | 180 minutes |
|---|---|---|---|---|---|---|---|
| A | 10g DL-BHB | 0.2 | 0.7 | 0.5 | 0.3 | 0.2 | 0.2 |
| B | 10g DL-BHB | 0.1 | 0.9 | 0.6 | 0.3 | 0.2 | 0.2 |
| C | 10g DL-BHB | 0.1 | 0.5 | 0.2 | 0.1 | 0.1 | 0.1 |
| D | 10g DL-BHB | 0.2 | 0.8 | 0.6 | 0.3 | 0.2 | 0.1 |
| Average | | 0.15 | 0.725 | 0.475 | 0.25 | 0.175 | 0.15 |
| A | 10g R-BHB | 0.2 | 1.8 | 0.7 | 0.4 | 0.3 | 0.2 |
| B | 10g R-BHB | 0.2 | 1.5 | 0.7 | 0.3 | 0.2 | 0.2 |
| C | 10g R-BHB | 0.1 | 0.7 | 0.3 | 0.2 | 0.2 | 0.1 |
| D | 10g R-BHB | 0.1 | 1.5 | 1.2 | 0.6 | 0.2 | 0.2 |
| Average | | 0.15 | 1.375 | 0.725 | 0.375 | 0.225 | 0.175 |
| A | 5g R-BHB | 0.3 | 0.6 | 0.3 | 0.4 | 0.3 | 0.4 |
| B | 5g R-BHB | 0.1 | 0.8 | 0.7 | 0.2 | 0.2 | 0.2 |
| C | 5g R-BHB | 0.1 | 0.4 | 0.2 | 0.2 | 0.2 | 0.1 |
| D | 5g R-BHB | 0.1 | 0.7 | 0.3 | 0.2 | 0.1 | 0.1 |
| Average | | 0.15 | 0.625 | 0.375 | 0.25 | 0.2 | 0.2 |

Figure 18A
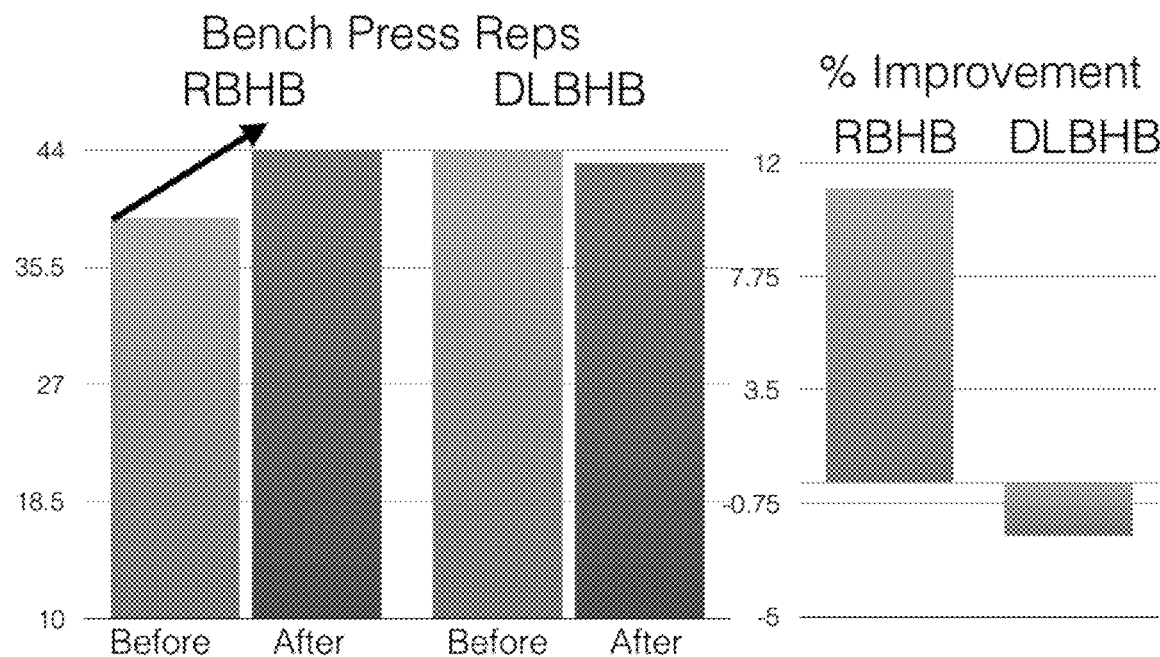
Figure 18B
Figure 18C
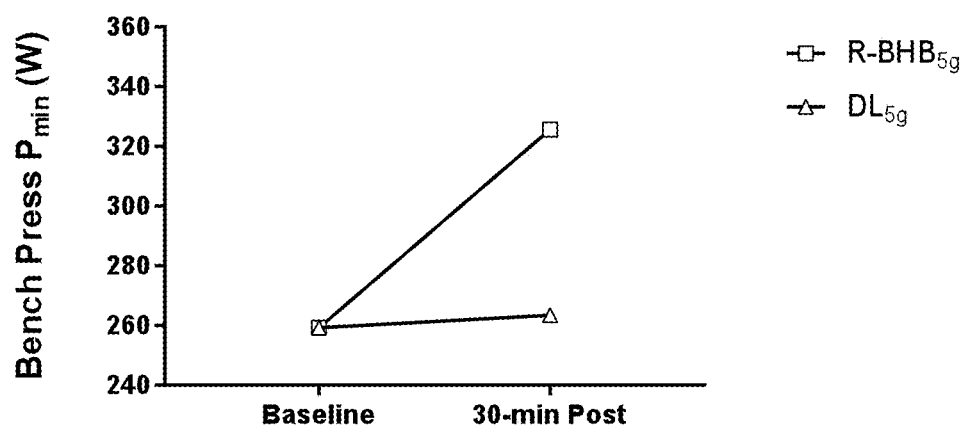

ADMINISTRATION OF BERBERINE METABOLITES

CROSS-REFERENCE TO RELATED APPLICATIONS

This application is a continuation of U.S. patent application Ser. No. 16/403,992, entitled "ADMINISTRATION OF BERBERINE M ETABOLITES", filed on May 6, 2019 and issued as U.S. Pat. No. 11,026,929, which is a continuation in part of U.S. patent application Ser. No. 15/491,933, entitled "ADMINISTRATION OF BERBERINE METABOLITES", filed on Apr. 19, 2017 and issued as U.S. Pat. No. 10,278,961, which claims the benefit of U.S. Provisional Patent Application No. 62/324,794, entitled "ADMINISTRATION OF DIHYDROBERBERINE", filed on Apr. 19, 2016, all of which are incorporated by reference for all purposes.

TECHNICAL FIELD

The present invention relates to managing metabolic and therapeutic functions by administering berberine metabolites.

BACKGROUND

Berberine is a naturally occurring substance commonly found in Goldenseal (*Hydrastis canadensis*), Oregon grape (*Berberis aquifolium*), Barberry (*Berberis vulgaris*), Chinese Goldthread (*Coptis chinensis, Phellodendron chinense*, and *Phellodendron amurense*. Berberine has been administered to humans and found to have an effect on inflammation and as well as having some antimicrobial properties. Berberine has also shown potential for lowering fasting blood glucose; however adverse gastrointestinal effects appeared to accompany the administration in amounts to effectively lower fasting blood glucose (Yin et al. "Efficacy of Berberine in Patients with Type 2 Diabetes," Metabolism. 2008 May; 57(5): 712-717). The bioavailability of traditional berberine has been shown in some studies to be below 70% in animal models which could affect how much is being absorbed and actually utilized in the body (Chen, W., Miao, Y. Q., Fan, D. J., Yang, S. S., Lin, X., Meng, L. K., & Tang, X. (2011). Bioavailability study of berberine and the enhancing effects of TPGS on intestinal absorption in rats. Aaps Pharmscitech, 12(2), 705-711.)

SUMMARY

In various implementations, one or more berberine metabolites (e.g., dihydroberberine and/or tetrahydroberberine) may be administered to manage glucose tolerance and/or increase ketones (e.g., blood concentration and/or urine concentration of ketones) in humans. For example, a pharmaceutically effective amount of berberine metabolites (e.g., dihydroberberine and/or tetrahydroberberine) may be administered to healthy and/or nonhealthy adults. For example a pharmaceutically effective amount of berberine metabolites may be administered to a human with diabetes or other metabolic disorder impacting glucose tolerance. The berberine metabolites may regulate glucose and/or lipid metabolism. In some implementations, administration of a pharmaceutically effective amount of berberine metabolites may be therapeutic to humans with diabetes, glucose intolerance, metabolic syndrome, dyslipidemia, and/or obesity/overweight. In some implementations, administration of berberine metabolites may have ergogenic (e.g., performance enhancing) and/or body composition benefits for some individuals (e.g., generally healthy; athletic; etc.) via glucose disposal, insulin sensitivity and ketone sensitivity. In some implementations, administration of berberine metabolite(s) may lower glycation (e.g., measured by HA1c levels) which may provide anti-aging properties.

In various implementations, the berberine metabolite composition administered to an individual may include dihydroberberine and/or tetrahydroberberine. For example, the composition may be orally administered in any appropriate delivery vehicle, such as via tablets, capsules, food products, and/or beverage products.

In some implementations, one or more berberine metabolites may be administered with one or more additional compounds. The additional compounds, such as ketone sensitizers, may be capable of independently inducing ketosis. The additional compounds may be utilized to maintain and/or promote ketosis in humans. For example, the additional compounds may include one beta-hydroxybutyrate compound; butyrate; short chain, medium chain, and/or long chain fatty acids or esters thereof, and/or combinations there of which may be administered with a berberine metabolite, such as dihydroberberine.

In various implementations, a pharmaceutically effective amount of dihydroberberine may be administered to an individual to managing glucose tolerance (e.g., decrease and/or maintain blood glucose level, decrease and/or maintain fasting blood glucose, increase ability to process glucose, etc.).

Implementations may include one or more of the following features. The administration of dihydroberberine may reduce fasting glucose levels. The dihydroberberine may be administered as a complexed composition. The complexed composition may include phytosomes and/or liposomes. The dihydroberberine may be a microemulsion including dihydroberberine. The pharmaceutically effective amount of dihydroberberine may include approximately 25 mg to approximately 800 mg of dihydroberberine, in some implementations. The dihydroberberine may be orally administered as a capsule, tablet, a food product, and/or beverage product. The dihydroberberine may be administered at least once daily (e.g., for a period of time, when desired by the user, etc.). In some implementations, a Cytochrome P450 inhibitor may be administered approximately concurrently. Administration of the Cyctochrome P450 inhibitor may allow decreasing of the amount of dihydroberberine administered to be sufficient to achieve the desired results (e.g., the same level of glucose management as a predetermined amount of dihydroberberine, a normal range of fasting glucose levels per health guidelines, normal level of blood glucose level per health guidelines, etc.).

In various implementations, administering, to an individual, a pharmaceutically effective amount of dihydroberberine may increase blood ketone levels.

Implementations may include one or more of the following features. The dihydroberberine may be administered approximately concurrently with meals. In some implementations, a pharmaceutically effective amount of an additional compound may be administered with the dihydroberberine, where the additional compound is capable of inducing ketosis independently (e.g., ketone sensitizer). The dihydroberberine and additional compound may be administered approximately concurrently. The dihydroberberine and additional compound may be administered at least one time daily (e.g., for a period of time, per user desire, per doctor recommendation, until glucose level and/or blood ketone level is within a predetermined range, etc.).

In various implementations, composition may be capable of maintaining ketosis in an individual (e.g., within a predetermined time period of administration to the individual). The composition may include a pharmaceutically effective amount of dihydroberberine and an additional compound (e.g., a compound that can impact blood ketone levels independently, such as a ketone sensitizer). The amount of dihydroberberine administered to be pharmaceutically effective may be less than the amount of dihydroberberine administered to be pharmaceutically effective when the dihydroberberine is administered without the additional compound(s) (e.g., to achieve a predetermined level of ketosis and/or a range of blood ketone levels).

Implementations may include one or more of the following features. The additional compound(s) may include beta-hydroxybutyrate (e.g., R-beta-hydroxybutyrate and/or D,L-beta-hydroxybutyrate), butyrate, fatty acid, and/or ester of fatty acid. The additional compound may include R-beta-hydroxybutyrate (e.g., salt, polymer, and/or complexed with another compound such as an amino acid). The additional compound may include a beta-hydroxybutyrate salt, beta-hydroxybutyrate polymer, beta-hydroxybutyrate amino acid (e.g., R-beta-hydroxybutyrate amino acid mixture and/or complex, such as R-beta-hydroxybutyrate and leucine), and/or beta-hydroxybutyrate free acid(s). The dihydroberberine and additional compound may be administered approximately concurrently. The dihydroberberine and additional compound may be a mixture and/or a complexed compound. The additional compound may include a beta-hydroxybutyrate and at least one of a fatty acid or ester of a fatty acid, in some implementations.

In various implementations, managing glucose tolerance in an individual may include administering, to an individual a pharmaceutically effective amount of a composition. The composition may include approximately 25 mg to approximately 800 mg of dihydroberberine; beta-hydroxybutyrate, and at least one of a fatty acid or ester of a fatty acid.

Implementations may include one or more of the following features. Administration of composition may at least one of reduces fasting glucose levels, promote ketosis, and/or maintains ketosis in the individual. The dihydroberberine may be administered as a complexed composition, and the complexed composition may include complexed phytosomes and/or liposomes. The dihydroberberine may include a microemulsion including dihydroberberine. The composition may be administered at least once daily. The compound may include a Cytochrome P450 inhibitor.

Administration of the Cyctochrome P450 inhibitor may allows decreasing of the amount of the composition administered to be sufficient to achieve the desired results. The beta-hydroxybutyrate may include R-beta-hydroxybutyrate and/or a mixture of R-beta-hydroxybutyrate and L-beta-hydroxybutyrate. The beta-hydroxybutyrate may include a beta-hydroxybutyrate salt and/or beta-hydroxybutyrate polymer. The fatty acid may include a medium chain fatty acid, a short chain fatty acid, and/or a long chain fatty acid. The fatty acid may include a medium chain fatty acid, a short chain fatty acid, and/or a long chain fatty acid such that an ester of the fatty acid may include ester of a medium chain fatty acid, ester of a short chain fatty acid, and/or ester of a long chain fatty acid. The at least one of a fatty acid or ester of a fatty acid comprises at least one of coconut oil, coconut butter, or coconut milk.

In various implementations, managing glucose tolerance in an individual may include administering, to an individual a pharmaceutically effective amount of a composition. The composition may include approximately 25 mg to approximately 800 mg of dihydroberberine and less than approximately 10 g of R-beta-hydroxybutyrate.

Implementations may include one or more of the following features. The administration of composition may promote and/or maintain ketosis in the individual. The R-beta-hydroxybutyrate may include at least 90 percent R-beta-hydroxybutyrate and less than 10 percent L-beta-hydroxybutyrate. The R-beta-hydroxybutyrate may include a beta-hydroxybutyrate salt and/or beta-hydroxybutyrate polymer. The composition may include one or more of additional compounds, such as a beta-hydroxybutyrate, a fatty acid, and/or ester of fatty acid. The additional compounds may include an additional beta-hydroxybutyrate salt and/or beta-hydroxybutyrate polymer.

In various implementations, managing glucose tolerance in an individual may include administering, to an individual a pharmaceutically effective amount of R-beta-hydroxybutyrate, wherein the pharmaceutically effective amount of R-beta-hydroxybutyrate includes less than approximately 2 g of R-beta-hydroxybutyrate.

Implementations may include one or more of the following features. The R-beta-hydroxybutyrate may include at least 90 percent R-beta-hydroxybutyrate and less than 10 percent L-beta-hydroxybutyrate. The R-beta-hydroxybutyrate may include a beta-hydroxybutyrate salt and/or beta-hydroxybutyrate polymer. The administration of composition may promote and/or maintain ketosis in the individual.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 2 illustrates a table of subject responsiveness to an example administration protocol.

FIG. 4 a table with blood ketone levels for subjects after administration of an example administration protocol.

FIG. 5 illustrates a table of blood ketone levels over time for 4 subjects for an implementation of an example administration of D,L-beta-hydroxybutyrate and R/D-beta-hydroxybutyrate.

FIG. 18A illustrates a chart illustrating strength test results following an implementation of an example administration protocol.

FIG. 18B illustrates a chart illustrating strength test results following an implementation of an example administration protocol.

FIG. 18C illustrates a chart illustrating power results following an implementation of an example administration protocol.

Like reference symbols in the various drawings indicate like elements.

DETAILED DESCRIPTION

Figure 1:
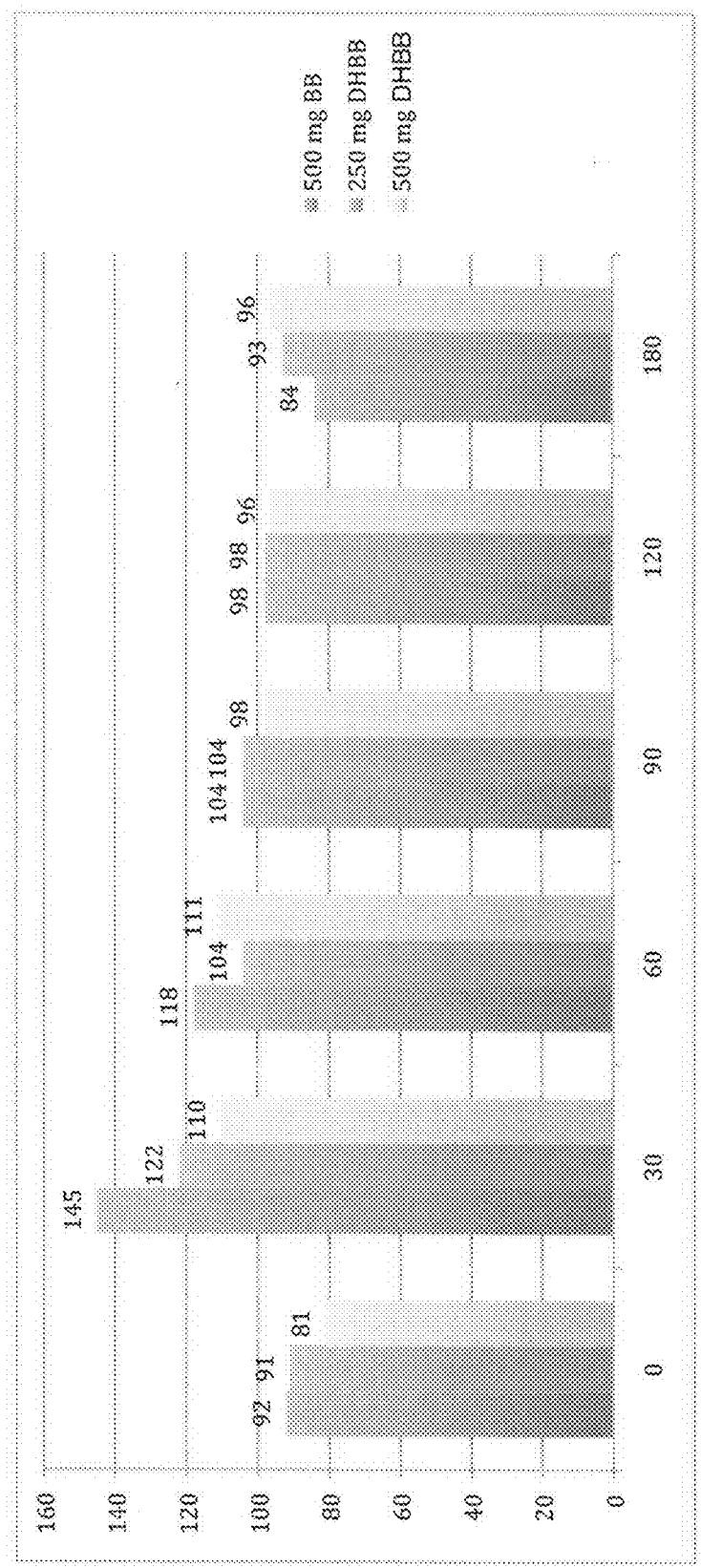
FIG. 1 illustrates table with glucose levels for subjects after administration of an example administration protocol.

In various implementations, administration of a pharmaceutically effective amount of berberine metabolites (e.g., dihydroberberine and/or tetrahydroberberine), derivates thereof and/or salts thereof may be administered to humans to manage blood glucose levels (e.g., reduce fasting blood glucose, improve glucose tolerance, etc.). In some implementations, administration of pharmaceutically effective amount of berberine metabolite(s) may maintain and/or increase ketone levels (e.g., blood and/or urine ketone concentration). In some implementations, administration of a pharmaceutically effective amount of berberine metabolite(s) (e.g., dihydroberberine and/or tetrahydroberberine) may be therapeutic to humans with diabetes, glucose intolerance, metabolic syndrome, dyslipidemia, and/or obesity/overweight. In some implementations, administration of berberine metabolites may have ergogenic (e.g., performance enhancing) and/or body composition benefits for some individuals (e.g., generally healthy; athletic; etc.) via glucose disposal, insulin sensitivity and ketone sensitivity. In some implementations, administration of a pharmaceutically effective amount of berberine metabolite(s) may lower glycation (e.g., measured by HA1c levels) which may provide anti-aging properties. The amount of berberine metabolite (e.g., dihydroberberine) administered to achieve a predetermined effect (e.g., fasting blood glucose level) may be less than the amount of berberine that would be required to achieve the same predetermined effect. In some implementations, one or more other compounds may be administered with the pharmaceutically effective amount of berberine metabolite, such as a ketone sensitizer (e.g., a compound that is capable of reducing and/or maintaining blood ketone levels independently, such as beta-hydroxybutyrate, short chain fatty acids, medium chain fatty acids, and/or long chain fatty acids).

In some implementations, a berberine metabolite composition may include dihydroberberine and/or tetrahydroberberine. Dihydroberberine ($C_{20}H_{19}NO_4$) is a compound that although related to berberine has properties that make it especially suited for managing glucose and/or increasing ketone levels (e.g., blood ketone levels). Dihydroberberine is a compound that is commercially available from sources such as, AdooQ Bioscience (Irving, CA).

Dihydroberberine may be more biologically available to humans than berberine. A first weight amount of dihydroberberine is capable of decreasing blood glucose levels greater than the same weight amount of berberine. A first weight amount of dihydroberberine may increase blood ketone levels more than the same weight amount of berberine. These are unexpected results since the inclusion of other function groups (hydro-) decreases the amount of "berberine" in the same weight amount of berberine. By increasing blood ketone levels, achieving a level of ketosis (e.g., blood ketone levels of 0.2 to 20 mM), maintaining a level of ketosis may be more easily obtainable during administration of dihydroberberine. Achieving ketosis may improve metabolic disorders, improve health (e.g., strength, mental acuity, etc.), increase weight loss, and/or increase fat loss (e.g., as opposed to lean muscle mass loss). Diabetes, various types of cancer, Alzheimer's, Parkinson's, Traumatic Brain Injury (TBI) PCOS, Metabolic Syndrome/Syndrome X, Obesity, Dyslipidemia, Aging, other metabolic disorders and/or other ketosensitive diseases and/or disorders may thus be affected by administration of dihydroberberine or tetrahydroberberine (e.g., since ketosis may be more easily achieved by individuals in which dihydroberberine has been administered).

In various implementations, the berberine metabolite may include tetrahydroberberine ($C_{20}H_{21}O_4N$). Tetrahydroberberine is a compound that although related to berberine has properties that make it especially suited for managing glucose and/or increasing ketone levels (e.g., blood ketone concentration). In some implementations, dihydroberberine and/or tetrahydroberberine may be complexed with other compounds such as phytosomes and/or liposomes. The berberine metabolite may be administered to a user via the complexed compound.

In various implementations, a pharmaceutically effective amount of berberine metabolite may be administered to humans to improve glucose tolerance. For example, an amount of approximately 25 mg to approximately 800 mg of dihydroberberine may be administered to a human. In some implementations, an amount of approximately 250 mg to approximately 300 mg may be administered to a human. The amount of dihydroberberine may be less than the amount of berberine required to achieve the same amount of glucose tolerance (e.g., a predetermined fasting glucose level, a predetermined range of blood glucose, a normal or other blood gluocose level as determined by health guidelines, a normal or other fasting blood glucose as determined by health guidelines, etc.). In some implementations, an amount of dihydroberberine may provide the same level of glucose tolerance as at least double the same amount of berberine (e.g., the dihydroberberine may be at least twice as effective as berberine and thus half or less than half of a first amount of dihydroberberine would be required to achieve the same results as the first amount of berberine). This result is unexpected since one would expect berberine and dihydroberberine to have similar properties. Even with the known increase bioavailability of dihydroberberine over berberine, the ability to administer as little as half as much dihydroberberine as berberine to achieve similar results in glucose tolerance is unexpected. The ability to reduce the quantity of dihydroberberine administered to a human may reduce the side effects associated with administration, ease palatability (e.g., since taste may improve or be more easily masked with smaller dosages), ease administration (e.g., smaller dose size), reduce costs, etc. For example, since the same amount (e.g., molecular amount) of the "berberine" group is in berberine and dihydroberberine, decreasing the amount administered would decrease side effects associated with administration of berberine and/or related complexes.

In various implementations, one or more additional compounds may be administered with the berberine metabolite. The additional compounds may increase a benefit of the berberine metabolite (e.g., glucose management, decrease ketone levels, etc.) and/or provide additional benefits (e.g., increase mental acuity, increase fat loss, increase lean mass maintenance, increase strength, etc.) For example, an additional compound that is capable of impacting blood ketone levels (e.g., increasing and/or maintaining blood ketone levels, inducing ketosis, etc.), such as a ketone sensitizer, may be selected that increases ketosis (e.g., increase levels of ketones bodies in the blood).

In some implementations, the additional compounds (e.g., ketone sensitizers) may include a beta-hydroxybutyrate compound may be administered with the berberine metabolite (e.g., in a capsule such as a softgel; tablet; powdered supplement; ready-to-drink formulation; topical product; cosmeceutical product; foods such bars, cookies, gum, candy, functional foods; toothpaste, sublingual product; injection; intravenous fluids; beverages such as shots or energy shots; inhalers and/or other appropriate administration methods). A beta-hydroxybutyrate compound may include beta-hydroxybutyrate salts, beta-hydroxybutyrate monomer, beta-hydroxybutyrate polymers, and/or combinations thereof. For example, beta-hydroxybutyrate salts may include sodium beta-hydroxybutyrate, magnesium beta-hydroxybutyrate, calcium beta-hydroxybutyrate, lithium beta-hydroxybutyrate, potassium beta-hydroxybutyrate and/or combinations thereof. In some implementations, beta-hydroxybutyrate polymers may be selected for administration with dihydroberberine to administer beta-hydroxybutyrate (e.g., since beta-hydroxybutyrate polymers are metabolized in the body to administer beta-hydroxybutyrate). In some implementations, the beta-hydroxybutyrate administered may include organic salts, such as but not limited to, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, and/or combinations thereof. The beta-hydroxybutyrate included in the composition may include R-beta-hydroxybutyrate (e.g., salts, polymers, complexes, etc.). The beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate.

In some implementations, the additional compound (e.g., that is capable of increasing blood ketone levels independently) may include a fatty acid and/or ester thereof. For example, the additional compound may include short chain, medium chain, and/or long chain fatty acids and/or esters thereof. The fatty acid(s) and/or esters thereof may include natural and/or synthesized compounds. For example, the additional compound may include coconut oil, butter, coconut milk, etc. The additional compound may be in any appropriate form (e.g., emulsion, liquid, powder, etc.).

In some implementations, the composition may include more than one additional compound that is capable of increasing blood ketone levels and/or inducing ketosis independently (e.g., without dihydroberberine). For example, a medium chain fatty acid may be administered with the berberine metabolite and/or beta-hydroxybutyrate compound. In some implementations, an amino acid may be administered with dihydroberberine and R-beta-hydroxybutyrate (e.g., salt, polymer, and/or complex).

In various implementations, a composition may be administered as described that includes berberine metabolites (e.g., Dihydroberberine, tetrahydroberberine, etc.) and/or an additional compound that increases ketone levels (e.g., blood and/or urine), such as a ketone sensitizer. The additional compound(s) may include one or more beta-hydroxybutyrate compounds, short chain triglycerides, medium chain triglycerides, long chain triglycerides, combinations thereof and/or derivatives thereof. For example, one or more of the beta-hydroxybutyrate compounds and/or other ketone sensitizers (e.g., short chain triglycerides, medium chain triglycerides, long chain triglycerides) in U.S. patent application Ser. No. 15/491,924, to Lowery et al. and entitled "Administration of Beta-hydroxybutyrate and Related Compounds in Humans", filed Apr. 19, 2017 and U.S. Provisional Patent Application No. 62/324,798, to Lowery et al. and entitled "Administration of Beta-hydroxybutyrate and Related Compounds in Humans", filed Apr. 19, 2016, which is incorporated by reference to the extent that the teachings do not conflict with the present disclosure, may be utilized as a ketone sensitizer.

To achieve a predetermined amount of ketosis in an individual, an amount of an additional compound (e.g., capable of increasing ketone levels and/or inducing ketosis independently) administered with berberine metabolite(s) (e.g., Dihydroberberine, tetrahydroberberine, etc.) may be less than an amount of the additional compound administered without dihydroberberine. In some implementations, when berberine metabolite(s) (e.g., Dihydroberberine, tetrahydroberberine, etc.) is administered, as blood glucose levels decrease, unexpectedly, blood ketone levels may rise. Thus, less of the additional compound may be administered to achieve a predetermined blood ketone level (e.g., to maintain and/or promote a state of ketosis). For example, an additional compound, such as 10 grams of sodium beta-hydroxybutyrate may be administered to a 200 pound human to achieve a first level of ketosis (e.g., blood ketone level of 0.5 mM). When dihydroberberine is administered, the amount of the additional compound may be decreased. For example, when 250 mg of dihydroberberine is administered to a 200 pound human, 3 milligrams of sodium beta-hydroxybutyrate may be administered to achieve the first level of ketosis rather than 10 grams of sodium beta-hydroxybutyrate. Administration of the additional compound (e.g., that is capable of independently increasing ketone levels and/or inducing ketosis) may cause increase user satisfaction (e.g., less side effects from increased amounts of the additional compound and/or cation when salts of the additional compounds are included) and/or decreases costs (e.g., since less of the additional compound may be utilized), and enhance endogenous production (e.g. since blood glucose is lower, endogenous ketones may be elevated alongside the exogenous ketones)

In some implementations, the berberine metabolite(s) (e.g., dihydroberberine tetrahydroberberine, etc.) and the additional compound (e.g., capable of increasing ketone levels in the blood) may be administered approximately concurrently. For example, the dihydroberberine and ketone sensitizer may be provided in a capsule, pill, granular form (e.g., packet of granules), powdered form, liquid, gel, sublingual, transdermal and/or any other appropriate administration form.

In some implementations, one or more additives may be included in the composition, such as flavorings (e.g., natural and/or artificial), vitamins, minerals, binders, and/or any other appropriate additive. The additives may alter flavor, color, and/or texture. The additives may increase palatability and/or facilitate inclusion in a delivery vehicle (e.g., tablet, food product, beverage product such as a drink mix, etc.).

In some implementations, the berberine metabolite(s) may be processed to increase bioavailability, solubility, palatability, and/or combination with other compounds. For example, berberine metabolite(s) may be processed to form a microemulsion with other compounds (e.g., ketone sensitizer, liposome, phytosome, flavorings, etc.). In some implementations, the berberine metabolite may be microencapsulated (e.g., with and/or without other compounds such as ketone sensitizer, liposome, phytosome). Microemulsions may improve bioavailability and solubility as well as other agglomeration technologies. The microencapsulated berberine metabolite(s) (e.g., with or without combination with other compounds) may be a free flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%), in some implementations. In some implementations, the berberine metabolite may be complexed with another compound (e.g., liposome, phytosome, and/or combinations thereof) and the berberine metabolite complex may be administered to the user to administer the berberine metabolite. Bioavailability enhancement via the mechanism of action for Cytochrome P450 inhibitors like naringen, bergamotin, piperine and its metabolites, as well as other bioavailability enhancers may be co-administered to enhance efficacy at lower therapeutic doses. Lowering the therapeutic dosage may decrease side effects and/or costs.

In various implementations, the berberine metabolite(s) (e.g., Dihydroberberine, tetrahydroberberine, etc.) and/or other compounds administered with the dihydroberberine may be administered on an appropriate administration schedule. For example, the Dihydroberberine/tetrahydroberberine and/or other compounds may be administered concurrently with meals, a predetermined amount of time before meals, a predetermined amount of time after meals, at regular or irregular time intervals, and/or according to other appropriate administration schedules. The berberine metabolite composition (e.g., including the berberine metabolite) may be administered on a periodic basis and/or as desired by a user. For example, the berberine metabolite composition may be administered to achieve a predetermined blood gluocose level and/or fasting level. The administration of the composition (e.g., in the same and/or lower dosage) may be continued and/or discontinued once the predetermined level is achieved. The berberine metabolite composition may be administered as desired by a user in some implementations (e.g., to facilite achieving user goals such as in strength training, for performance, for insurance testing, etc.). In some implementations, the amount of Dihydroberberine/tetrahydroberberine and/or other compounds administered at each dose may be the same and/or different.

In some implementations, the composition administered to an individual (e.g., human and/or any other appropriate animal) may include approximately 5 mg to approximately 1 gram of dihydroberberine. The composition may include one or more other compounds that may or may not be capable of increasing blood ketone levels independently, in some implementations. The composition may be administered (e.g., orally) approximately 1 to approximately 3 times daily. In some implementations, the composition may be provided in a delivery form such powder (e.g., that capable consumed separately, mixed with drinks, and/or food) and/or tablet. The administration of the composition may maintain ketosis levels for approximately 30 min to approximately 3 hours. The administration of the composition may maintain ketosis for longer than 3 hours. The administration of the composition may maintain blood glucose levels within a healthy range (e.g., as determined by a doctor, health guidelines, insurance guidelines, etc.). The administration of the composition may decreases blood glucose levels during a glucose challenge testing by over 25%, in some implementations. The administration of the composition may be capable of maintaining approximately 2 to approximately 3 times greater elevated ketones during carbohydrate intake (e.g., when compared with berberine and/or when compared with individuals not being administered dihydroberberine). The administration of the composition may increased fat metabolism by 10% (e.g., when compared with the individuals capability without administration of dihydroberberine).

In some implementations, the compound may include dihydroberberine and a beta-hydroxybutyrate. The composition may include one or more other compounds that may or may not be capable of increasing blood ketone levels independently, in some implementations. The composition may include approximately 5 mg to approximately 1 g of dihydroberberine and approximately 2 g of beta-hydroxybutyrate to approximately 10 g of beta-hydroxybutyrate. In some implementations, the composition may include approximately 400 mg to approximately 600 mg of dihydroberberine (e.g., approximately 500 mg) and approximately 4 to approximately 7 g of beta-hydroxybutyrate (e.g., 5 g of beta-hydroxybutyrate, such as R-beta-hydroxybutyrate). The composition may be administered (e.g., orally) approximately 1 to approximately 3 times daily. In some implementations, the composition may be provided in a delivery form such powder (e.g., that capable consumed separately, mixed with drinks, and/or food) and/or tablet. The combination of dihydroberberine and additional compounds that are capable of increasing ketones independently, such as beta-hydroxybutyrate, may increase ketones at a greater level than the expected additive amount. For example, a composition of 500 mg of dihydroberberine and 5 grams of beta-hydroxybutyrate and 5 grams of short chain triglyceride may increase ketones over 1 mM (e.g., while 5 grams of BHB alone elevate blood ketone levels to only 0.5 mM)

In some implementations, the dihydroberberine may be complexed or otherwise coupled to one or more of the additional compounds in the composition. For example, the composition may include a dihydroberberine-beta-hydroxybutyrate complex and/or a dihydroberberine-amino acid complex.

In some implementations, administration of dihydroberberine may maintain and/or improve memory functions, cognitive functioning, brain health, telomere health, and/or combinations thereof. Administration of dihydroberberine may improve and/or maintain mood and/or psychological health. Administration of dihydroberberine may provide neuroprotection. Administration of dihydroberberine may promote longevity. For example, administration of approximately 25 mg to approximately 800 mg of dihydroberberine may improve brain health (e.g., memory, cognitive function, general health, telomere health, etc.). In some implementations, other additional compounds (e.g., fatty acids, esters of fatty acids, beta-hydroxybutyrate, R-beta-hydroxybutyrate), as previously described, may be administered with the dihydroberberine.

In various implementations, dihydroberberine may be utilized independently and/or in conjunction with additional compounds to manage glucose tolerance, reducing fasting glucose levels; maintain and/or promote ketosis (e.g., maintain and/or increase blood ketone levels); and/or promote and/or maintain weight loss. As a nonlimiting example, dihydroberberine, beta-hydroxybutyrate, and at least one of a fatty acid or an ester of a fatty acid may be administered to manage glucose tolerance, reducing fasting glucose levels, and/or maintain and/or promote ketosis (e.g., maintain and/or increase blood ketone levels). In some implementations, the individual may be administered dihydroberberine, beta-hydroxybutyrate, and a triglyceride. As a nonlimiting example, dihydroberberine and R-beta-hydroxybutyrate may be administered to manage glucose tolerance, reducing fasting glucose levels, and/or maintain and/or promote ketosis (e.g., maintain and/or increase blood ketone levels). As a nonlimiting example, R-beta-hydroxybutyrate may be administered to manage glucose tolerance, reducing fasting glucose levels, and/or maintain and/or promote ketosis (e.g., maintain and/or increase blood ketone levels). In some implementations, at least approximately 25 mg and less than approximately 800 mg of dihydroberberine may be administered. The dihydroberberine may be any appropriate form of dihydroberberine. In some implementations, at least approximately 0.1 g and less than approximately 15 mg of beta-hydroxybutyrate may be administered. The beta-hydroxybutyrate may include racemic mixtures and/or individual isomers of betahydroxy-butyrate (e.g., approximately 100% R-beta-hydroxybutyrate; 90% R-beta-hydroxybutyrate and 10% L-beta-hydroxybutyrate; at least 90% R-beta-hydroxybutyrate and less than 10% L-beta-hydroxybutyrate). In some implementations, salts, polymers, esters, complexes, or combinations thereof of beta-hydroxybutyrate may be administered. At least 0.1 g and less than 50 g of fatty acid and/or ester of fatty acid (e.g., triglyceride) may be administered. The fatty acids and/or esters may include natural (e.g., cream, coconut oil, macadamia oil, etc.) and/or artificial fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid.

In some implementations, dihydroberberine, beta-hydroxybutyrate, and at least one of a fatty acid or an ester of a fatty acid may be administered to manage glucose tolerance, reducing fasting glucose levels, and/or maintain and/or promote ketosis (e.g., maintain and/or increase blood ketone levels). In some implementations, the individual may be administered dihydroberberine, beta-hydroxybutyrate, and a triglyceride.

In some implementations, dihydroberberine and R-beta-hydroxybutyrate may be administered to manage glucose tolerance, reducing fasting glucose levels, and/or maintain and/or promote ketosis (e.g., maintain and/or increase blood ketone levels).

In some implementations, R-beta-hydroxybutyrate may be administered to manage glucose tolerance, reducing fasting glucose levels, and/or maintain and/or promote ketosis (e.g., maintain and/or increase blood ketone levels). As described in herein and in U.S. patent application Ser. No. 15/491,924, to Lowery et al. and entitled "Administration of Beta-hydroxybutyrate and Related Compounds in Humans", which is incorporated by reference to the extent that the teachings do not conflict with the present disclosure, R-beta-hydroxybutyrate may be administered to increase and/or maintain glucose tolerance and/or ketosis (e.g., increase and/or maintain blood ketone levels). In some implementations, administration of R-beta-hydroxybutyrate may promote and/or maintain weight loss. The R-beta-hydroxybutyrate may include L-beta-hydroxybutyrate, in some implementations. For example, the composition administered may include at least approximately 90% R-beta-hydroxybutyrate and less than 10% approximately L-beta-hydroxybutyrate. In some implementations, one or more additional compounds, as described herein and in U.S. patent application Ser. No. 15/491,924 may be administered with the R-beta-hydroxybutyrate to maintain glucose tolerance, decrease fasting glucose, promote ketosis, maintain ketosis, promote weight loss, and/or maintain weight loss.

In various implementations, compounds such as butyrate, beta-hydroxybutyrate and/or related compounds (e.g., derivatives, esters, polymers, etc.) can be administered alone or in combination with one or more other compounds. Administration of a pharmaceutically effective amount of these compound(s) may promote and/or maintain weight loss and/or ketosis. In some implementations, blood ketone levels and/or blood glucose levels may be reduced and/or maintained within a predetermined range when a pharmaceutically effective amount of one or more compounds are administered. In some implementations, a health of an individual (e.g., strength, symptoms of disease, mental acuity, fasting glucose levels, etc.) may be improved and/or maintained by administration of a compound that includes butyrate, beta-hydroxybutyrate and/or related compounds (e.g., derivatives, esters, polymers, etc.).

In various implementations butyrate, beta-hydroxybutyrate and/or related compounds may be administered to a human. Beta-hydroxybutyrate (e.g., R-beta-hydroxybutyrate, L-beta-hydroxybutyrate, and/or D,L-beta-hydroxybutyrate) may include beta-hydroxybutyrate salts and/or beta-hydroxybutyrate esters. In some implementations, beta-hydroxybutyrate may include beta-hydroxybutyrate bound to another compound (e.g., amino acids) and/or polymers of beta-hydroxybutyrate. For example, beta-hydroxybutyrate (e.g., R-beta-hydroxybutyrate, L-beta-hydroxybutyrate, and/or D,L-beta-hydroxybutyrate) may include beta-hydroxybutyrate salts, beta-hydroxybutyrate esters, beta-hydroxybutyrate sodium salt (e.g., sodium beta-hydroxybutyrate), beta-hydroxy butyrate potassium salt (e.g., potassium beta-hydroxybutyrate), beta-hydroxybutyrate calcium salt (e.g., calcium beta-hydroxybutyrate), beta-hydroxybutyrate magnesium salt (e.g., magnesium beta-hydroxybutyrate), beta-hydroxybutyrate lithium salt (e.g., lithium beta-hydroxybutyrate), sodium beta-hydroxybutyrate, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, or citrulline beta-hydroxybutyrate, other appropriate organic salts that include beta-hydroxybutyrate, and/or combinations thereof. In some implementations, the beta-hydroxybutyrate may include beta-hydroxybutyrate salts including (calcium, sodium, magnesium, potassium, zinc, selenium, chromium, other appropriate minerals, and/or combinations thereof. In some implementations, the beta-hydroxybutyrate may be complexed and/or coupled to another compound (e.g., amino acid and/or berberine) and a beta-hydroxybutyrate salt may include a complex (e.g., chelate) that includes a mineral (e.g., calcium, zinc, etc.) and the beta-hydroxybutyrate compound coupled to another compound. The beta-hydroxybutyrate may include single isomer beta-hydroxybutyrate and/or polymer beta-hydroxybutyrate. For example, R-beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate.

The beta-hydroxybutyrate may include racemic mixtures and/or individual isomers of betahydroxy-butyrate. In some implementations, one or more specific chiralities of beta-hydroxybutyrate may be utilized. For example, R-beta-hydroxybutyrate (also referred to as D-beta-hydroxybutyrate), S-beta-hydroxybutyrate (also referred to as L-beta-hydroxybutyrate), and/or mixtures (e.g., raecemic mixtures) thereof may be utilized. In some implementations, R-beta-hydroxybutyrate may be included in the composition (e.g., a more purified form of R-beta-hydroxybutyrate rather than D,L-beta-hydroxybutyrate). For example, R-beta-hydroxybutyrate may include less than approximately 10 percent, less than approximately 5 percent, or less than approximately 1 percent L-beta-hydroxybutyrate. R-beta-hydroxybutyrate may have a greater bioavailability than other chiralities of beta-hydroxybutyrate. R-beta-hydroxybutyrate may have a greater impact on a health of an individual (e.g., due to decreased side effects; increase ketone levels, weight loss, mental acuity, fat loss, etc.) than L-beta-hydroxybutyrate and/or D,L-beta-hydroxybutyrate. In some implementations, R-beta-hydroxybutyrate may cause improvements in health not capable by L-beta-hydroxybutyrate and/or D,L-beta-hydroxybutyrate. R-beta-hydroxybutyrate may have less impurities due to manufacturing, such as less crotonic acid (e.g., which can be harmful to individuals), than other forms of beta-hydroxybutyrate (e.g., L-beta-hydroxybutyrate and/or D,L-beta-hydroxybutyrate). In some implementations, R-beta-hydroxybutyrate may be more capable of binding with other compounds (e.g., purine, lysine, potassium, and/or other amino acids; dihydroberberine; etc.) to deliver the beta-hydroxybutyrate to a human. Thus, R-beta-hydroxybutyrate (e.g., greater than 90 percent purity of R-beta-hydroxybutyrate and less than 10 percent L-beta-hydroxybutyrate) and/or mixtures with R-beta-hydroxybutyrate may be administered to humans. In some implementations, unexpectedly, a smaller amount of R-beta-hydroxybutyrate may be as pharmaceutically effective (e.g., in increasing and/or maintaining weight loss; in increasing and/or maintaining elevated ketone levels, etc.) or more pharmaceutically effective as D,L-beta-hydroxybutyrate (e.g., raecemic mixture of D- and L-beta-hydroxybutyrate). For example, approximately half an amount of R-beta-hydroxybutyrate may be administered to achieve the approximately the same efficacy as D,L-beta-hydroxybutyrate and/or L-beta-hydroxybutyrate. The R-beta-hydroxybutyrate may be more bioavailable than other chiralities of beta-hydroxybutyrate and thus allow a smaller effective amount than other chiralities. Thus, by utilizing R-beta-hydroxybutyrate, the administration amount of beta-hydroxybutyrate to be reduced (e.g., when compared to the administration amount of D,L-beta-hydroxybutyrate) while providing a pharmaceutically effective amount, such as (e.g., for weight loss and/or maintenance; for elevating and/or maintaining blood ketone levels). Reducing the amount of beta-hydroxybutyrate, when the beta-hydroxybutyrate is provided in salt form, may reduce a user's intake of the cation of the salt (e.g., sodium, potassium, etc.). Since intake of some of these cations in beta-hydroxybutyrate salts, such as sodium, potassium, magnesium, and calcium, in amounts greater than a predetermined recommended amount may cause health problems (e.g., organ damage, gastrointestinal problems, etc.), reducing the amount of beta-hydroxybutyrate salt by using R-beta-hydroxybutyrate may inhibit side effects and/or health problems associated salts combined with beta-hydroxybutyrate administration in users.

In some implementations, a pharmaceutically effective amount of R-beta-hydroxybutyrate may be administered in an individual to promote and/or maintain ketosis, cause weight loss and/or manage weight, and/or increase blood ketone levels. For example, approximately 0.1 g to approximately 50 g of R-beta-hydroxybutyrate may be administered to an individual. In some implementations, approximately 0.1 g to approximately 15 g of R-beta-hydroxybutyrate may be administered to an individual. In some implementations, approximately 1 g to approximately 10 g of beta-hydroxybutyrate may be administered, for example, once a day to 5 times a day (e.g., to administer up to 50 g of beta-hydroxybutyrate). The administration may cause weight loss and/or maintenance; elevated beta-hydroxybutyrate levels in the blood; elevated, reduced, and/or maintenance of blood ketone levels; induction and/or maintenance of ketosis; and/or reduction; improve mental acuity; improve focus; improve energy; improve cognitive function; reduce traumatic brain injury; improve diabetes; improve gluocose tolerance; decrease blood glucose levels; reduce neurological disorders and/or symptoms thereof, improve cancer and/or symptoms thereof, improve inflammatory conditions; suppressing appetite; improve symptoms associated with aging; provide anti-glycation affects; improve epilepsy and/or symptoms thereof; improve depression and/or symptoms thereof, improve performance; improve strength; increase muscle mass; increase fat loss; improve body composition; improve energy; improve focus; improve cognitive function; improve mood and/or well-being; and/or combinations thereof. The beta-hydroxybutyrate (e.g., R-beta-hydroxybutyrate) may be administered in healthy and not healthy individuals (e.g., individuals with diseases and/or disorders).

In some implementations, the beta-hydroxybutyrate, such as R-beta-hydroxybutyrate, may be administered with and/or coupled to a compound such as an amino acid. For example beta-hydroxybutyrate may be coupled to (e.g., chemically bonded to) amino acids, such as leucine, lysine, arginine, histidine, ornithine, creatine, agmatine, citrulline and/or combinations thereof. In some implementations, R-beta-hydroxybutyrate may be utilized rather than other chiralities since R-beta-hydroxybutyrate may be more easily bound to leucine, purine, lysine, and/or other amino acids. Administration of beta-hydroxybutyrate that is coupled to an amino acid may reduce the intake of cations associated with beta-hydroxybutyrate salts (e.g., which may inhibit side effects associated with administration) and/or allow administration of another compound that has health benefits (e.g., administration of some amino acid may promote smooth muscle growth and/or cell repair). In some implementations, approximately 0.5 g to approximately 10 g of amino acid may be administered with a beta-hydroxybutyrate. For example, less than approximately 50 g of R-beta-hydroxybutyrate and less than approximately 60 mg of an amino acid, such as leucine, may be administered daily. In some implementations, approximately 0.5 g to approximately 2 g of an amino acid, such as leucine, may be administered with a beta-hydroxybutyrate. For example, approximately the composition administered may include approximately 0.1 to approximately 7 g R-beta-hydroxybutyrate and approximately 1-3 g of leucine. The R-beta-hydroxybutyrate and the leucine may be a mixture; administered separately and proximate in timing; a complex, and/or administered in any other appropriate manner.

In some implementations, the composition may include R-beta-hydroxybutyrate salt and beta-hydroxybutyrate-amino acid complex (e.g., beta-hydroxybutyrate bound to amino acid, such as R-beta-hydroxybutyrate-leucine complex). For example, an individual may be administered a first weight amount of sodium beta-hydroxybutyrate and a second weight amount of beta-hydroxybutyrate amino-acid complex. The first amount and the second amount may be different or the same.

In some implementations, the beta-hydroxybutyrate composition may include beta-hydroxybutyrate salt and beta-hydroxybutyrate esters. For example, an individual may be administered a first weight amount of sodium beta-hydroxybutyrate and a second weight amount of beta-hydroxybutyrate ester. The first amount and the second amount may be different or the same. The beta-hydroxybutyrate salt and the beta-hydroxybutyrate ester may be a bound complex, a mixture of compounds, and/or separately administered approximately concurrently. In some implementations, the beta-hydroxybutyrate ester may be in powdered form (e.g., plated beta-hydroxybutyrate ester), liquid and/or gel form. The combination of beta-hydroxybutyrate salt and beta-hydroxybutyrate ester during administration may allow less salt to be utilized while producing a result (e.g., weight maintenance and/or loss; enhanced and/or maintained ketosis; elevated blood ketone levels; blood glucose reduction and/or maintenance; increase in energy; increase in mood; increase in performance; and/or increase in cognitive function). In some implementations, elevated ketone levels (e.g., elevated blood ketone levels) may increase energy, mood, performance, and/or cognitive function in users. For example, the administration of the first amount of beta-hydroxybutyrate salt may cause a first level of blood ketone level, which may be maintained by processing of the second amount of the beta-hydroxybutyrate ester (e.g., as the body of the individual processes the beta-hydroxybutyrate ester the level of beta-hydroxybutyrate in the blood, and thus blood ketone level, may also increase over time to enhance and/or maintain the initial elevation caused by of the administered beta-hydroxybutyrate salt). For example, a ratio of beta-hydroxybutyrate to beta-hydroxybutyrate ester may be approximately 1 beta-hydroxybutyrate salt:approximately 1 beta-hydroxybutyrate ester to approximately 1 beta-hydroxybutyrate salt:approximately 20 beta-hydroxybutyrate ester. The ratio of beta-hydroxybutyrate to beta-hydroxybutyrate ester may be approximately 20 beta-hydroxybutyrate salt:approximately 1 beta-hydroxybutyrate ester to approximately 1 beta-hydroxybutyrate salt:approximately 20 beta-hydroxybutyrate ester. In some implementations, a ratio of beta-hydroxybutyrate to beta-hydroxybutyrate ester may be approximately 1 beta-hydroxybutyrate salt:approximately 1 beta-hydroxybutyrate ester to approximately 1 beta-hydroxybutyrate salt:approximately 5 beta-hydroxybutyrate ester.

Related compounds that may be included as beta-hydroxybutyrate in the composition may include derivatives of beta-hydroxybutyrate, include esters of (R)-3-hydroxybutyrate and oligomers of (R)-3-hydroxybutyrate. For example, beta-hydroxybutyrate esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate may include structures of (R)-3-hydroxybutyric acid and an exemplary ester thereof (a glycerol monoester). The R chirality of the derivatives may be selected for inclusion in the composition in some implementations (e.g., to deliver R-beta-hydroxybutyrate with the administration of the compound).

In some implementations, butyrate, beta-hydroxybutyrate (e.g., R-beta-hydroxybutyrate), related compounds, and/or combinations thereof may be administered along with one or more additional compounds. The additional compounds may or may not be capable of independently increasing ketone levels, maintaining ketone levels, inducing ketosis, and/or maintaining ketosis. For example, additional compounds capable of independently increasing blood ketone levels may include short chain fatty acids (e.g., fatty acid with between 2 carbons than 6 carbons), short chain triglycerides (e.g., triglycerides with less than 6 carbons), medium chain fatty acids (e.g., fatty acid with 6-12 carbons), medium chain triglycerides (e.g., triglycerides with 7-12 carbons), long chain fatty acids (e.g., fatty acids with more than 12 carbons), long chain triglycerides (e.g., triglycerides with more than 12 carbons), and/or combinations thereof. In some implementations, short chain fatty acids and/or triglycerides may include acetate, propionate, and/or butyrate. Medium chain fatty acids and/or triglycerides may include lauric acid and/or coconut oil, coconut milk powder, fractionated coconut oil, isolated hexanoic acid, isolated octanoic acid, isolated decanoic acid, ethoxylated triglyceride, triglyceride derivatives thereof, aldehyde triglyceride derivatives thereof, monoglyceride derivatives thereof, diglyceride derivatives thereof, triglyceride derivatives thereof, and/or alkyl esters thereof. Long chain fatty acids and/or triglycerides may include dairy products and/or palm oil. In some implementations, a compound including R-beta-hydroxybutyrate and an additional compound that is independently capable of increasing ketone levels may increase ketone levels greater than merely the capability of each component individually (e.g., greater than an additive increase).

For example, a pharmaceutically effective amount of one or more short chain fatty acids and/or one or more short chain triglycerides (e.g., butyric acid and/or butyrate) may be administered with a pharmaceutically effective amount of beta-hydroxybutyrate. In some implementations, approximately 1 g to approximately 10 g of beta-hydroxybutyrate and approximately 0.1 g to approximately 50 g of short chain fatty acid and/or triglyceride may be administered from once a day to approximately 5 times a day. In some implementations, approximately 1 g to approximately 3 g of beta-hydroxybutyrate and approximately 1 g of short chain fatty acid and/or triglyceride may be administered from once a day to approximately 5 times a day. In some implementations, the short chain fatty acid and/or triglyceride may include butyrate or derivatives of butyrate. Butyrate and/or derivatives of butyrate may be administered with and/or without beta-hydroxybutyrate to manage metabolic conditions, such as ketosis, and/or for other appropriate therapeutic purposes. Administered butyrate may be converted to beta-hydroxybutyrate in humans, and thus may increase the amount of beta-hydroxybutyrate delivered to the user. In some implementations, administration of butyrate and beta-hydroxybutyrate may promote hGH synthesis, improve basal and GHRH-induced hGH-secretion, increase muscle fiber cross-sectional area, inhibit intramuscular fat accumulation; reduce fat mass in a user; improve glucose metabolism; increase markers of mitochondrial biogenesis in skeletal muscle and/or whole-body oxygen consumption; reduced markers of oxidative stress and apoptosis and altered antioxidant enzyme activity; cause butyrate enhanced intracellular free cytosolic calcium levels (e.g., by acting through GPR41 and 43); increase beta-hydroxybutyrate levels; and/or support barrier function(s) in the gut and/or reduce inflammation associated with ulcerative colitis. Since butyrate is processed by the body to provide beta-hydroxybutyrate, the delivery of beta-hydroxybutyrate via the butyrate may supplement the directly administered beta-hydroxybutyrate to maintain a level of beta-hydroxybutyrate in the blood (e.g., to promote ketosis, weight loss and/or management, etc.).

However, butyrate and/or butyric acid may not be palatable to individuals (e.g., since the odor and taste are often compared to vomit). Thus, in some implementations, butyrate and/or beta-hydroxybutyrate (e.g., R-beta-hydroxybutyrate) may be processed to reduce organoleptic reactions. For example, the butyrate and/or beta-hydroxybutyrate (e.g., R-beta-hydroxybutyrate) may be encapsulated, microemulsion, liposomes, agglomeration, masking/flavoring technologies, and/or otherwise processed as appropriate to reduce organoleptic reactions from individuals administered the described composition(s). In some implementations, microencapsulated butyrate, beta-hydroxybutyrate, and/or butyric acid may be utilized (e.g., in combination with beta-hydroxybutyrate). Using microencapsulated butyrate, beta-hydroxybutyrate, and/or butyric acid (e.g., when compared with using unencapsulated forms) may increase individual satisfaction and/or compliance with an administration schedule since odor from the butyrate and/or butyric acid may be reduced and/or removed. The microencapsulated butyrate, beta-hydroxybutyrate, and/or butyric acid may be a free flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%).

In some implementations, a pharmaceutically effective amount of butyrate may be administered via triglyceride tributyrin (e.g., glyceryl tributyrate or tributyrin). The butyrate via triglyceride tributyrin may be administered separately and/or in conjunction with one or more of the other described compounds (e.g., beta-hydroxybutyrate, fatty acids and/or esters, etc.). For example, up to approximately 200 mg/kg of the individual may be administered (e.g., up to 3 times daily). Administration of the tributyrin may allow a delayed release of butyrate to the body as the tributyrin is processed by the body of the individual. The tributyrin may be unencapsulated and/or encapsulated (e.g., microencapsulated).

In some implementations, administration of beta-hydroxybutyrate and a short chain compound (e.g., short chain fatty acid and/or short chain triglyceride) may unexpectedly increase beta-hydroxybutyrate concentrations in the blood more than the administration of similar amounts of beta-hydroxybutyrate and medium chain compounds (e.g., short chain fatty acid and/or short chain triglyceride) and/or may increase beta-hydroxybutyrate concentrations in the blood more than each component individually.

In some implementations, a pharmaceutically effective amount of beta-hydroxybutyrate may be administered with a pharmaceutically effective amount of long chain fatty acid and/or triglyceride. For example, 0.1-50 g of beta-hydroxybutyrate and 0.1 to 50 g of long chain fatty acid may be administered to an individual between 1-5 times a day. In some implementations, approximately 1 g to approximately 3 g of beta-hydroxybutyrate and approximately 1 g of long chain fatty acid and/or triglyceride may be administered from once a day to approximately 5 times a day.

In some implementations, beta-hydroxybutyrate, short chain compound(s) (e.g., fatty acids and/or triglycerides, butyrate), and/or medium chain compound(s) (e.g., fatty acids and/or triglycerides) may be administered approximately simultaneously and/or sequentially to an individual. For example, approximately 0.1 g to approximately 50 g beta-hydroxybutyrate, approximately 0.1 g to approximately 50 g short chain triglyceride, and approximately 0.1 g to approximately 50 g medium chain fatty acid such as lauric acid and/or coconut oil may be administered between 1-5 times a day. In some implementations, approximately 1 g to approximately 3 g of beta-hydroxybutyrate and approximately 1 g of short chain fatty acid and/or triglyceride and/or approximately 1 g of medium chain fatty acid and/or triglyceride may be administered from once a day to approximately 5 times a day. In some implementations, approximately 0.1 g to approximately 20 g beta-hydroxybutyrate (e.g., salts, esters, isomers, and/or other appropriate forms) may be administered in humans. In some implementations, approximately 0.1 g to approximately 20 g butyrate may be administered in humans.

In some implementations, other compounds, such as compounds capable of independently decreasing glucose levels, may be administered with beta-hydroxybutyrate, such as berberine and/or associated metabolites (e.g., dihydroberberine and/or tetrahydroberberine). U.S. patent application Ser. No. 15/491,933 entitled "ADMINISTRATION OF DIHYDROBERBERINE" to Lowery et al, filed Apr. 19, 2017 and U.S. Provisional Patent Application No. 62/324,794, entitled "ADMINISTRATION OF DIHYDROBERBERINE" to Lowery et al, filed Apr. 19, 2016, describe dihydroberberine administration with ketone sensitizers such as beta-hydroxybutyrate, and is hereby fully incorporated herein. In some implementations, one or more beta-hydroxybutyrates and/or other compounds described herein may be utilized as a ketone sensitizer with the dihydroberberine.

In some implementations, directly administering beta-hydroxybutyrate plus another compound that is processed to deliver beta-hydroxybutyrate (e.g., beta-hydroxybutyrate ester, beta-hydroxybutyrate polymer, butyrate, other appropriate compounds, and/or combinations thereof) over time may allow a first level of beta-hydroxybutyrate in the blood to be maintained over a period of time. For example, since the directly administered beta-hydroxybutyrate may elevate blood beta-hydroxybutyrate levels to a first concentration and this concentration may be approximately maintained over a period of time by providing additional beta-hydroxybutyrate via another compound administered approximately concurrently (e.g., short chain fatty acid and/or triglyceride, beta-hydroxybutyrate ester, beta-hydroxybutyrate polymer, beta-hydroxybutyrate amino acid complex, etc.).

In some implementations, one or more other compounds may be administered (e.g., included in the composition and/or separately administered) with the butyrate (e.g., microencapsulated butyrate), beta-hydroxybutyrate (e.g., R-beta-hydroxybutyrate) and/or fatty acids or esters, such as short chain fatty acids. Other compositions may include, but are not limited to amino acids, amino acid metabolites, vitamins, minerals, coconut milk powder, flavorings, colorings, binders, electrolytes, tetrahydrobiopeterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid and ascorbate salts, citric acid, malic acid, sodium benzoate, Pyridoxal-5-Phosphate, methylcobalamin, cyanocobalamin, adenosylcobalamin, hydroxycobalamin, pantothenic acid, pantetheine, potassium sorbate, acesulfame K, aspartame, sucralose, stevia, monk fruit extract, allulose, prebiotic fibers, XOS, GOS, MOS, IMO, LOS, xanthan gum and other organic gums/thickeners/suspension agents, and combinations thereof.

In various implementations, administration of a composition that includes beta-hydroxybutyrate may improve the health of an individual. R-beta-hydroxybutyrate may be capable of providing a greater impact on the health of an individual than D,L-beta-hydroxybutyrate and/or L-beta-hydroxybutyrate. Although previously unknown, L-beta-hydroxybutyrate may decrease the effectiveness of R-beta-hydroxybutyrate with respect to at least a portion of the impact on health. With respect to some impacts on health, L-beta-hydroxybutyrate may have no impact on health. In some implementations, even double the amount of D,L-beta-hydroxybutyrate may not achieve some of the same results (e.g., in health improvement) as R-beta-hydroxybutyrate. Thus, unexpectedly administration of D,L-beta-hydroxybutyrate rather than R-beta-hydroxybutyrate may not have the same impact on health and/or have less of an impact on health of an individual. For example, administration of a composition that includes R-beta-hydroxybutyrate (e.g., and/or other compounds) may improve and/or maintain an individual's health.

Administration of R-beta-hydroxybutyrate as described may increase lifespan in individuals following a dietary plan (e.g., standard American low-fat, ketogenic, Paleo, Mediterranean, etc.) and/or not following a dietary plan. For example, approximately 10 g of R-beta-hydroxybutyrate to approximately 30 g R-beta-hydroxybutyrate may be administered to increase lifespan. In some implementations, other appropriate amounts of R-beta-hydroxybutyrate may be included in the composition.

In some implementations, administration of R-beta-hydroxybutyrate may treat and/or lessen the impact of symptoms of disease(s) and/or disorders, such as diseases that impact cognitive function. Administration of R-beta-hydroxybutyrate may increase motor function in individuals with Parkinson's disease. For example, approximately 5 g of R-beta-hydroxybutyrate to approximately 15 g R-beta-hydroxybutyrate may be administered to increase motor function. In some implementations, other appropriate amounts of R-beta-hydroxybutyrate may be included in the composition.

Administration of R-beta-hydroxybutyrate may increase fat loss. Unlike with conventional diets, in which weight loss often comes from decreases in water retention and/or muscle mass, administration of R-beta-hydroxybutyrate may cause decreases in fat loss (see for example, FIG. 9B). In addition, administration of R-beta-hydroxybutyrate may decrease levels of LPL in the body, and thus reduce or inhibit fat storage and/or encourage existing fat storage utilization by the body. For example, approximately 1 g of R-beta-hydroxybutyrate to approximately 20 g R-beta-hydroxybutyrate may be administered to cause fat loss and/or reduce fat storage. In some implementations, other appropriate amounts of R-beta-hydroxybutyrate may be included in the composition. Administration of R-beta-hydroxybutyrate may allow fat loss greater than 5 kg while maintaining lean mass. In some implementations, the administration of R-beta-hydroxybutyrate increases the amount of fat used as fuel.

In some implementations, administration of R-beta-hydroxybutyrate may improve and/or maintain health markers such as C-reactive protein and/or fasting glucose. Administration of R-beta-hydroxybutyrate may decrease inflammation (e.g., as shown by C-reactive protein levels). Administration of R-beta-hydroxybutyrate may decrease fasting glucose. For example, approximately 3 g of R-beta-hydroxybutyrate to approximately 20 g R-beta-hydroxybutyrate may be administered to cause a reduction in and/or maintain a low fasting glucose. In some implementations, other appropriate amounts of R-beta-hydroxybutyrate may be included in the composition. In some implementations, R-beta-hydroxybutyrate may be administered with one or more other compounds to decrease glucose levels and/or sensitivity. For example, administration of a composition of R-beta-hydroxybutyrate and a berberine, such as dihydroberberine, may cause reduce and/or maintain low fasting glucose. Administration of a composition of R-beta-hydroxybutyrate and a berberine, such as dihydroberberine, may cause reduce and/or maintain low glucose levels. In some implementations, less than approximately 15 g of R-beta-hydroxybutyrate may be administered with less than approximately 600 mg of dihydroberberine.

Administration of R-beta-hydroxybutyrate may decrease ketone levels (see e.g., FIGS. 11A and 11B). Decreasing blood ketone levels may increase weight loss, maintain weight loss, improve performance, increase mental acuity, and/or have other health improvement and health maintenance features. For example, even at levels less than 10 g (e.g., approximately 5 g), administration of R-beta-hydroxybutyrate may decrease ketone levels while L-R-beta-hydroxybutyrate does not, and D,L-beta-hydroxybutyrate does not to the same extent. R-beta-hydroxybutyrate may increase blood ketone levels 5 times as much as similar administration amounts of D,L-beta-hydroxybutyrate. By being able to decrease an amount of R-beta-hydroxybutyrate (e.g., when compared with administering D,L-beta-hydroxybutyrate) administered and achieve the same results, a decrease in an amount cation (e.g., sodium, potassium, etc.) may also be administered. Since some individuals may prefer and/or may not tolerate higher dosages of the cations of the R-beta-hydroxybutyrate salt, utilizing R-beta-hydroxybutyrate may allow administration to more people, increase user satisfaction, and/or decrease side effects (e.g., associated with additional consumption of these cations). In some implementations, approximately 0.1 g of R-beta-hydroxybutyrate to approximately 10 g R-beta-hydroxybutyrate may be administered to increase blood ketone levels. Approximately 0.5 g of R-beta-hydroxybutyrate to approximately 3 g R-beta-hydroxybutyrate may be administered to maintain blood ketone levels. In some implementations, other appropriate amounts of R-beta-hydroxybutyrate may be included in the composition.

Administration of R-beta-hydroxybutyrate may increase performance and decrease perceived exertion (e.g., as opposed to when administered D,L-beta-hydroxybutyrate). For example, approximately 3 g of R-beta-hydroxybutyrate to approximately 15 g R-beta-hydroxybutyrate may be administered to increase performance and/or decrease perceived exertion. In some implementations, other appropriate amounts of R-beta-hydroxybutyrate may be included in the composition.

In various implementations, oral administration of R-beta-hydroxybutyrate may increase muscle protein synthesis while D,L-beta-hydroxybutyrate does not increase muscle protein synthesis. For example, approximately 10 g of R-beta-hydroxybutyrate to approximately 30 g R-beta-hydroxybutyrate may be administered to increase muscle protein synthesis. In some implementations, other appropriate amounts of R-beta-hydroxybutyrate may be included in the composition.

In some implementations, the administration of R-beta-hydroxybutyrate, unlike D,L-beta-hydroxybutyrate may decrease perceived hunger and/or increase satiety) which may inhibit overeating and thus promote weight loss (see e.g., FIGS. 13A and 13B). In some implementations, the administration of R-beta-hydroxybutyrate, unlike D,L-beta-hydroxybutyrate may increased perceived energy (see e.g., FIG. 13C).

In some implementations, administration of R-beta-hydroxybutyrate increased mental acuity. For example, approximately 0.1 g of R-beta-hydroxybutyrate to approximately 10 g R-beta-hydroxybutyrate may be administered to increase mental acuity. In some implementations, other appropriate amounts of R-beta-hydroxybutyrate may be included in the composition.

In some implementations, the administration of R-beta-hydroxybutyrate may be supplemented with other forms of beta-hydroxybutyrate, butyric acid, and/or butyrate.

In some implementations, the composition administered may include R-beta-hydroxybutyrate. The amount of R-beta-hydroxybutyrate included in the composition may be selected to obtain a result (e.g., induce ketosis; maintain ketosis; increase ketone levels, mental acuity, strength, etc.) upon administration (e.g., a pharmaceutically effective amount may be administered at a dosage and/or over a predetermined time period). In some implementations, the dosage and/or frequency of dosage may vary over time (e.g., initial vs a lower dosage for maintenance, vary based on time of day, vary based on whether taken with or without a meal, etc.).

The R-beta-hydroxybutyrate in the composition may include any appropriate and/or appropriate number of forms, such as salts, derivatives (e.g., esters), polymers, and/or complexes with other compounds. For example, the composition may include R-beta-hydroxybutyrate salt (e.g., sodium R-beta-hydroxybutyrate, magnesium R-beta-hydroxybutyrate, and/or potassium R-beta-hydroxybutyrate) and/or another form of R-beta-hydroxybutyrate (e.g., ester, polymer, complex, etc.). In some implementations, the composition may include an ester of R-beta-hydroxybutyrate. The composition may include an amino acid (e.g., separate and/or complexed with R-beta-hydroxybutyrate), such as leucine. The use of non-salt base R-beta-hydroxybutyrate may increase user satisfaction (e.g., by reducing the cation, such as sodium and/or potassium, load due to ingestion of the composition; by decreasing side effects; etc.), increase the applicability of the administration (e.g., since users sensitive to the cations of the R-beta-hydroxybutyrate salts may be less sensitive to the non-salt and/or lower salt plus non-salt forms of the composition). The administration of the composition may increase blood ketone levels, induce ketosis, maintain blood ketone levels, maintain ketosis, increase health, increase strength, increase mental acuity, etc. In some implementations, a first composition that includes R-beta-hydroxybutyrate salt may be administered to cause a first impact (e.g., induce ketosis, quickly increase mental acuity, quickly increase strength, etc.) and a second composition that includes non-salts R-beta-hydroxybutyrate (e.g., esters, polymers, complexes, etc.) and/or lower levels of R-beta-hydroxybutyrate salt may be utilized to cause a second impact (e.g., maintain ketosis, maintain mental acuity, maintain increased strength, etc.).

In some implementations, the form(s) of R-beta-hydroxybutyrate included in the may be selected based on the delivery form. For example, in some forms of food products the composition may include R-beta-hydroxybutyrate polymer (e.g., due to taste since increased cations like sodium may decrease palatability; due to nutrition since increased cations such as sodium may decrease nutrition; due to mixability, etc.). As another example, the composition may include R-beta-hydroxybutyrate salts or other forms (e.g., microencapsulated) to provide quick dissolve powders.

In various implementations, a composition may include R-beta-hydroxybutyrate. The R-beta-hydroxybutyrate may be in any appropriate form (e.g., salt, ester, polymer, complex, derivatives thereof, and/or combinations thereof). The composition may include one or more additional compositions. Additional composition(s) may be capable of independently increasing blood ketone levels (e.g., fatty acids or esters, berberine or berberine metabolites such as dihydroberberine, etc.). Additional composition(s) may be capable of independently decreasing blood glucose levels (e.g., berberine or berberine metabolites such as dihydroberberine). In some implementations, additional compounds may not be capable of independently increasing blood ketone levels and/or decreasing blood glucose levels (e.g., additives, flavorings, colorings, minerals, vitamins, binders, anti-caking agents, etc.). The composition may be administered in an effective amount to cause a predetermined health impact (e.g., predetermined level of ketosis, blood ketone level, mental acuity, strength increase, perceived energy, fat loss, weight loss, etc.). The composition may be administered to an individual in a predetermined amount and/or different amounts over an administration schedule. In some implementations, once a first criteria is satisfied (e.g., period of time, number of doses, predetermined health impact), the dosage amount may be altered. For example, first dose(s) of the composition may be administered to cause a predetermined health impact and additional lower dose(s) of the composition may be administered to maintain the predetermined health impact (e.g., caused in part by the first doses).

The composition may be administered in any appropriate delivery form (e.g., tablet; capsule; food products such as powdered products that can be mixed into food, mixed into beverages, and/or consumed directly; beverage product; etc.). The composition may be administered according to any appropriate schedule (e.g., periodic dosages, dosages as user desires, etc.). The administration schedule may inhibit administration that elevates blood ketone levels too high, decreases blood glucose levels too low, and/or causes an individual to consume a dosage that substantially elevates the risk of adverse and/or side effects, in some implementations.

In some implementations, the composition may include a long acting component and/or be long-acting. For example, since the body digests polymers and/or esters of beta-hydroxybutyrate (e.g., R-beta-hydroxybutyrate), the delivery of R-beta-hydroxybutyrate may be slower than a digestion of a beta-hydroxybutyrate salt (e.g., R-beta-hydroxybutyrate salt). In some implementations, the composition may include a R-beta-hydroxybutyrate and a long acting R-beta-hydroxybutyrate form (e.g., polymer, ester, coated and/or processed form to provide slow release). In some implementations, a first dose(s) may include at least one non-long acting form of beta-hydroxybutyrate and a second dose(s) may include at least one long-acting form of beta-hydroxybutyrate. The first dose(s) may be administered to cause a predetermined health impact and the second dose(s) may be administered to maintain the caused predetermined health impact. In some implementations, users may select the appropriate dose based on user preference and/or properties (e.g., a user on a ketogenic diet may chose the second dose since the user may already be in ketosis).

EXAMPLE

Example 1

Five subjects were subject to three separate glucose challenge tests (75 g glucose) after administration of 500 mg berberine (BB), 250 mg of dihydroberberine (DHBB) or 500 dihydroberberine. Blood was drawn prior to administration and after 30, 60, 90, 120, and 180 minutes. FIG. 1 illustrates the results of the administration protocol. FIG. 1 illustrates the average blood glucose level of the 5 subjects at each of the times.

As illustrated, unexpectedly, administration of the dihydroberberine resulted in less fluctuations in blood glucose level than berberine. In addition, an unexpected result of the administration of dihydroberberine is that administration of dihydroberberine may keep blood glucose levels closer to fasting blood glucose than berberine.

Example 2

As in Example 1, five subjects were subject to three separate glucose challenge tests (75 g glucose) after administration of 500 mg berberine (BB), 250 mg of dihydroberberine (DHBB) or 500 dihydroberberine. FIG. 2 illustrates a ranking which compositions caused the lowest blood glucose levels during a oral glucose challenge. Unexpectedly, 250 mg of DHBB may control blood glucose levels better than even 500 mg of DHBB. For example, in some individuals (e.g., individuals with moderate glucose tolerance) may achieve better blood glucose control when administered a lower dosage of DHBB. As illustrated, dihydroberberine administration resulted in lower blood glucose than administration of berberine in most individuals.

Example 3

Figure 3:
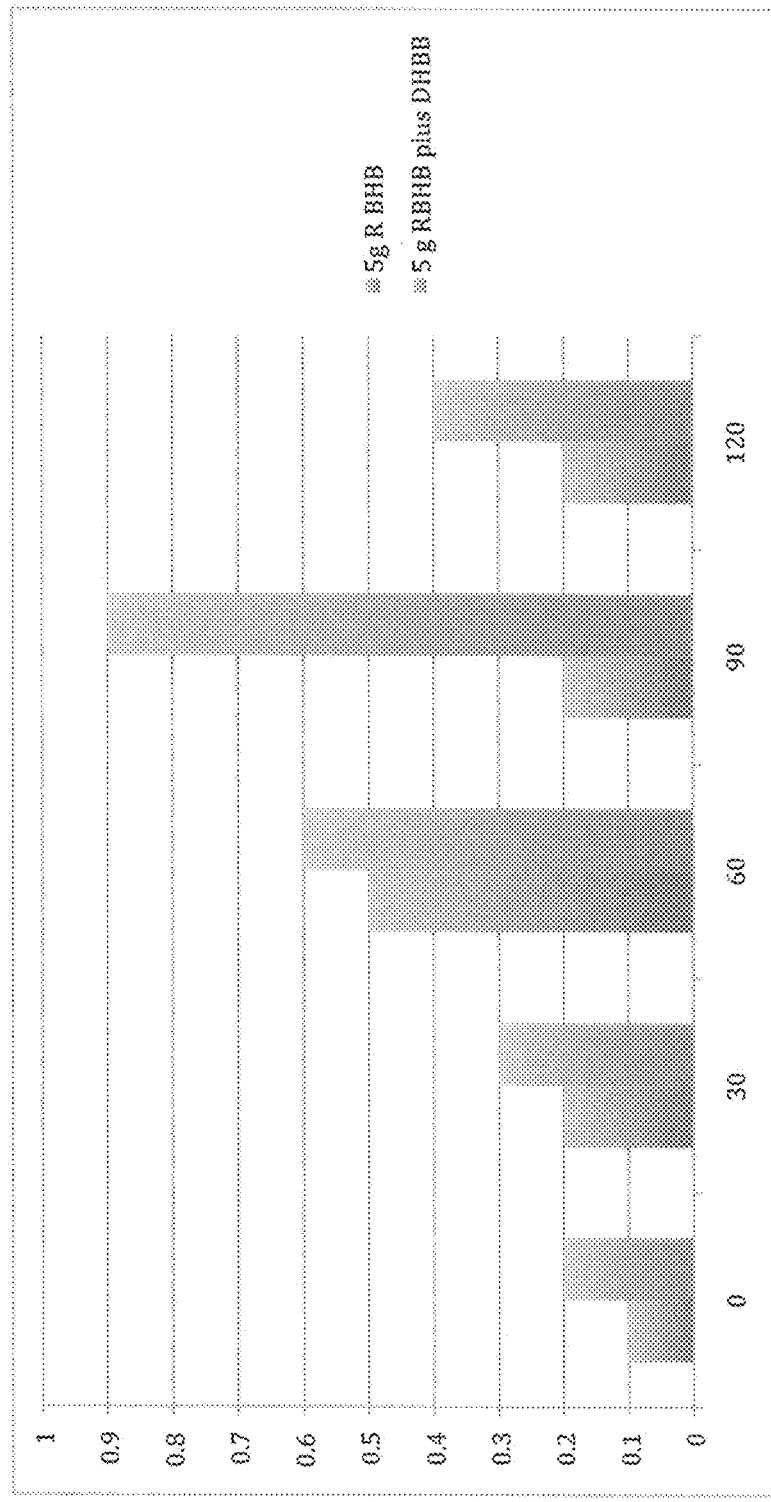
FIG. 3 illustrates a table with blood ketone levels for subjects after administration of an example administration protocol.

A subject was subject to a glucose challenge test (75 g glucose) after administration of 250 mg dihydroberberine (DHBB) and a glucose challenge test after administration of 250 mg dihydroberberine (DHBB) along with 5 mg of beta-hydroxybutyrate (e.g., 5 mg sodium beta-hydroxybutyrate). As illustrated in FIG. 3, blood ketone levels are unexpectedly increased even 120 minutes after the glucose challenge with the administration of an effective amount of dihydroberberine.

Example 4

Figure 4:
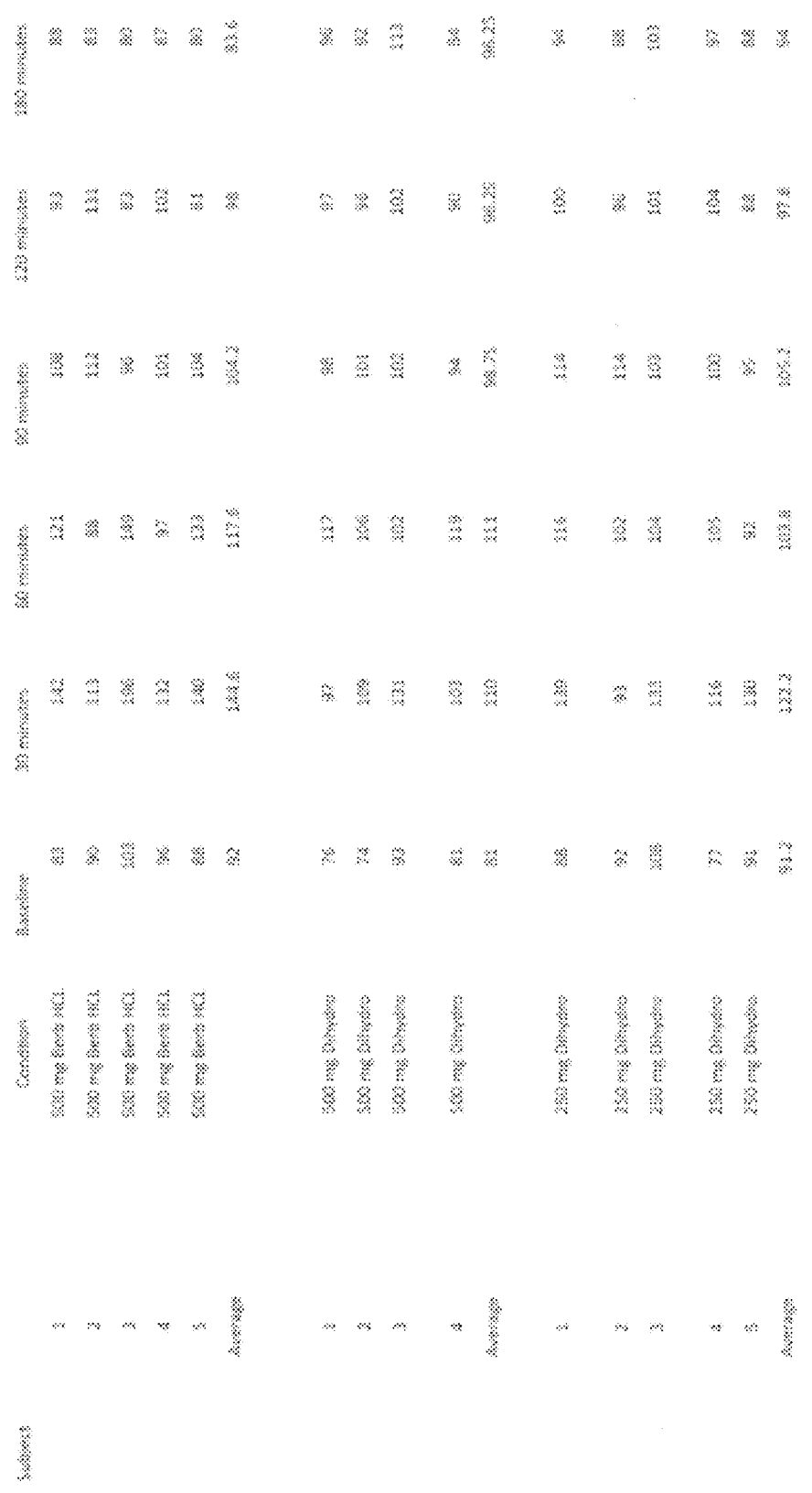

Five subjects were subject to three separate glucose challenge tests (75 g glucose) approximately 25 minutes after administration of 500 mg berberine (BB), 250 mg of dihydroberberine (DHBB) or 500 dihydroberberine. Blood was drawn prior to administration and after 30, 60, 90, 120, and 180 minutes and tested for glucose levels. FIG. 4 illustrates the results of the administration protocol.

As illustrated, administration of dihyroberberine in individuals with moderate baseline glucose levels moderates blood glucose levels better than even double the quantity of berberine.

Example 5

4 subjects were administered 10 mg of sodium D,L-beta-hydroxybutyrate and their blood ketone level in mmol/dL was tested after administration, 30 minutes, 60 minutes, 90 minutes, 120 minutes, and 180 minutes after administration. Each subject was also subsequently studied after administration of 10 g of sodium R-beta-hydroxybutyrate and 5 g of sodium R-beta-hydroxybutyrate. As illustrated in FIG. 5, on average, administration of 5 mg of sodium R-beta-hydroxybutyrate produced approximately the same blood ketone level in a subject after 30 minutes, 60 minutes, 90 minutes, 120 minutes, and 180 minutes as 10 g of D,L-beta-hydroxybutyrate.

Example 6

Figure 6:
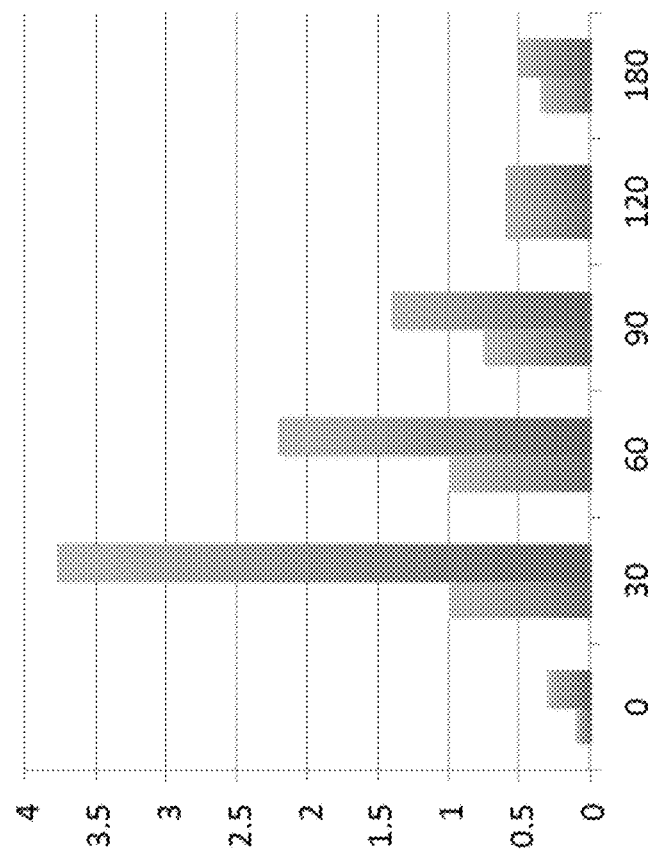
FIG. 6 illustrates a table of blood ketone levels over time for an implementation of an example administration of the microencapsulated butyrate compared to traditional sodium butyrate.

Three subjects were administered 10 grams of medium chain triglycerides and 8 grams of beta-hydroxybutyrate and blood beta-hydroxybutyrate concentration was monitored over time. The same subjects were later administered 10 grams of short chain triglycerides and 8 grams of beta-hydroxybutyrate and blood beta-hydroxybutyrate concentration was monitored. FIG. 6 illustrates an average blood ketone concentration (mmol/L) for the subjects after administration, after 30 minutes, after 60 minutes, after 90 minutes, after 120 minutes, and after 180 minutes. As illustrated in FIG. 6, administration of the beta-hydroxybutyrate with a short chain compound (illustrated in red bars or the second bar in each set), such as short chain triglyceride, caused greater elevation of blood ketone levels than administration of a similar amount of medium chain compound (illustrated in the blue bars or first bar in each set) at least after administration, after 30, 60, 90 minutes, and 180 minutes. Thus, administration of short chain compounds (e.g., fatty acids and/or triglycerides) may unexpectedly allow a smaller weight amount, when compared to medium chain compounds, to be administered to produce the same result (e.g., blood ketone level, weight loss, weight management, etc.) and/or allow greater results (e.g., when compared with similar amount of medium chain compounds).

Example 7

Figure 7:
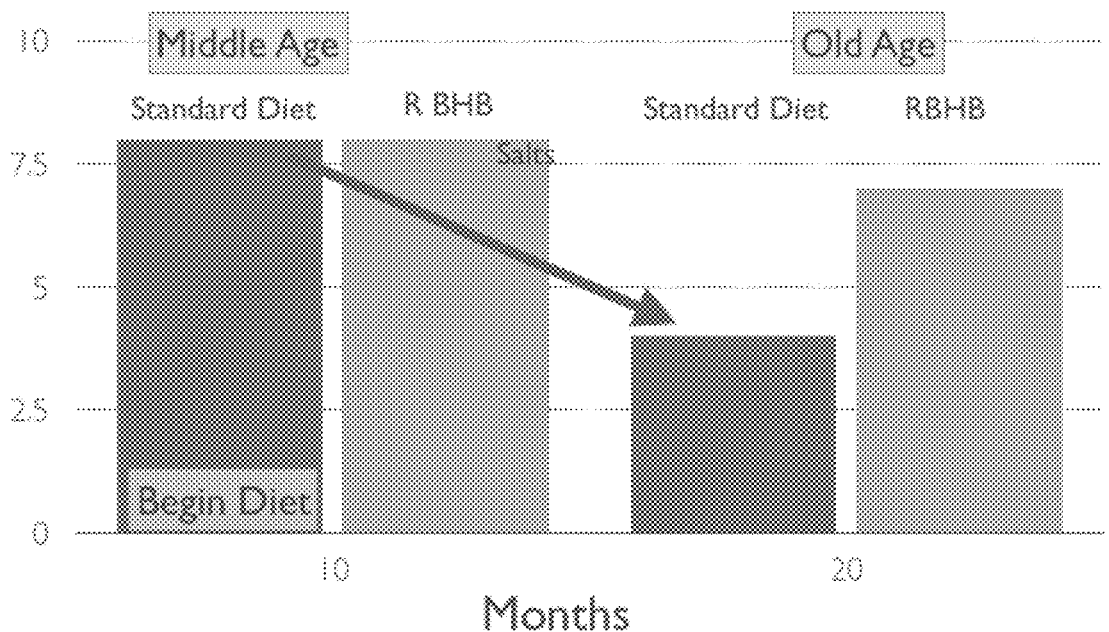
FIG. 7 illustrates a chart including lifespan of rats subject to an implementation of an administration of R-beta-hydroxybutyrate.

Sixteen rats (Fischer 344 rats) were studied for the effect of R-beta-hydroxybutyrate on lifespan. A first grouping of eight rats were fed an equivalent to a low-fat standard American diet and a second grouping of eight rats were fed the same equivalent to a low-fat standard American diet and supplemented with R-beta-hydroxybutyrate salt (e.g., sodium R-beta-hydroxybutyrate). The second grouping of rats were supplemented with the R-beta-hydroxybutyrate salt at middle age. FIG. 7 illustrates the average lifespans of the groupings of rats. As illustrated, at 20 months approximately half of the first grouping of rats died on the standard diet while only 12.5% of the second grouping of rats had died at 20 months. Thus, the supplementation of rats diets with R-beta-hydroxybutyrate increased lifespan for approximately in at least approximately 38.5% of the rats. Since the rat study was performed as an approximation of impact in humans, the addition of R-beta-hydroxybutyrate to a standard American low-fat diet may increase lifespan.

Example 8

An individual with Parkinson's disease was tested for motor function with and without administration of approximately 10 g of R-beta-hydroxybutyrate salt. The testing included a right-eye visual and motor performance apparatus to track motor function through eye movements.

Figure 8:
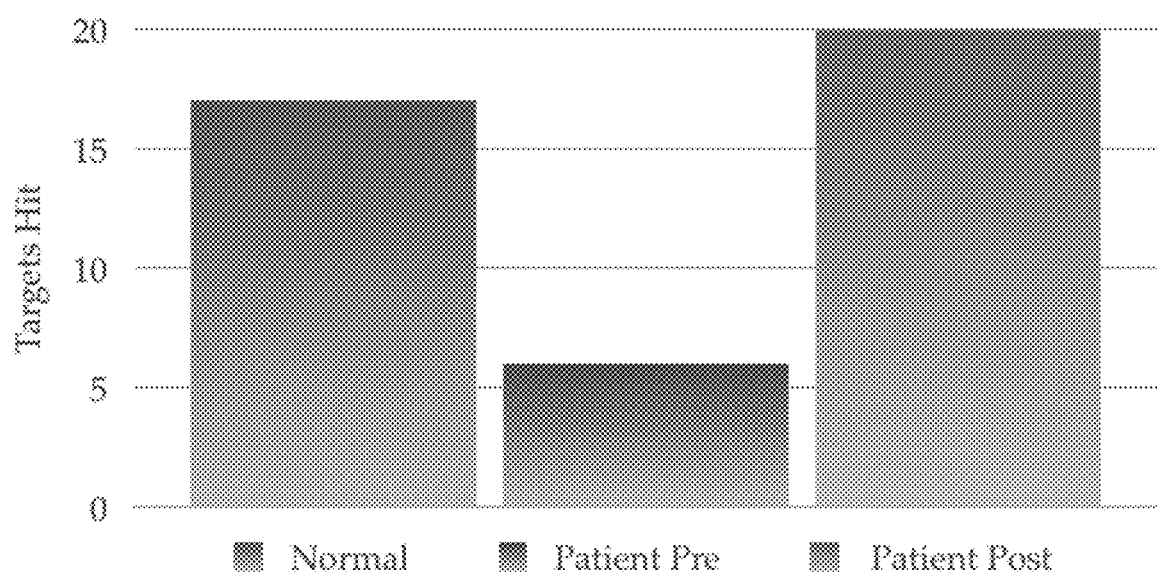
FIG. 8 illustrates a chart illustrating the results of motor skill testing following an implementation of an example administration protocol.

FIG. 8 illustrates chart illustrating the results of the motor skill testing following an example implementation of administration of R-beta-hydroxybutyrate. FIG. 8 illustrates average results for a similar non-Parkinson's population, the patient pre-administration of R-beta-hydroxybutyrate, and the patient post-administration of R-beta-hydroxybutyrate. As illustrated, the administration of R-beta-hydroxybutyrate increased motor function (e.g., approximately 30 minutes after administration of the R-beta-hydroxybutyrate).

Example 9

Figures 9A, 9B:
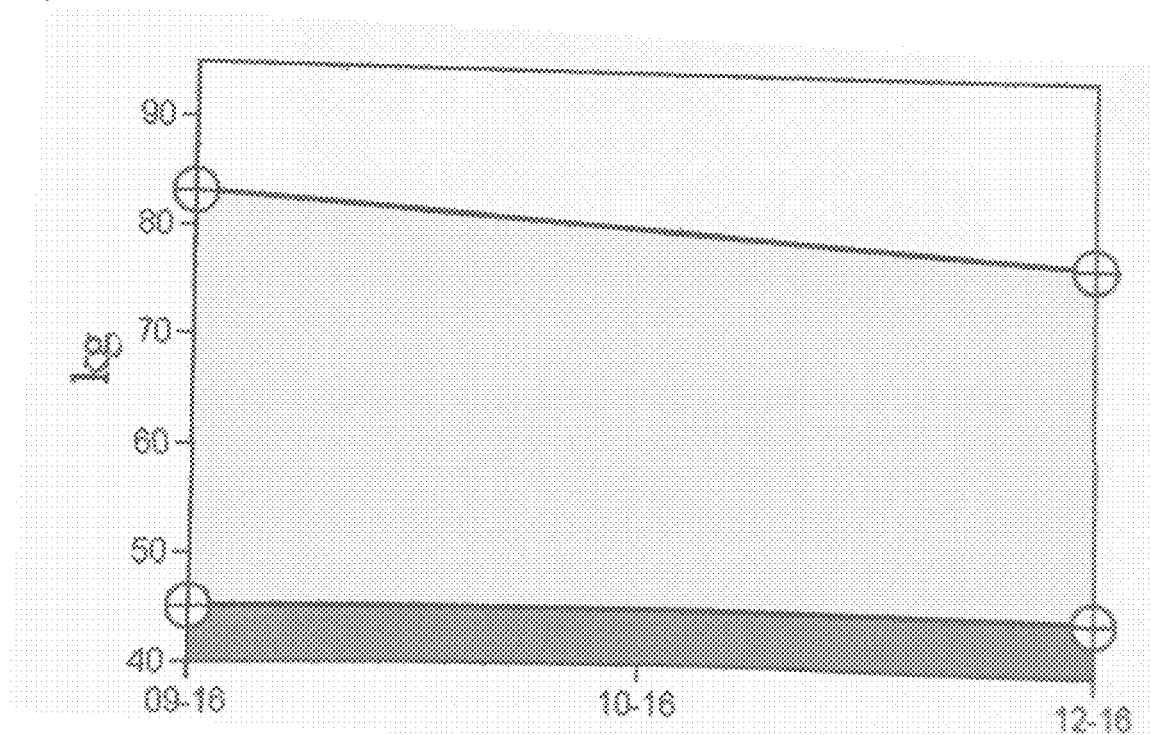
FIG. 9A illustrates a chart illustrating fat loss results following an implementation of an example administration protocol.
FIG. 9B illustrates a chart illustrating fat mass and lean mass results following an implementation of an example administration protocol.

An individual was administered 5 g of R-beta-hydroxybutyrate twice daily for 3 months. Xray absorptiometry was performed to determine the impact of the administration of R-beta-hydroxybutyrate on fat loss. FIG. 9A illustrates a chart that shows the results after 3 months of administration. As illustrated, the individual experienced a greater than approximately 10% decrease in fat mass. FIG. 9B illustrates that the fat loss was sustained while maintaining lean mass. Thus, the R-beta-hydroxybutyrate may cause weight loss through fat loss rather than lean mass (e.g., muscle mass).

Example 10

Figure 10:
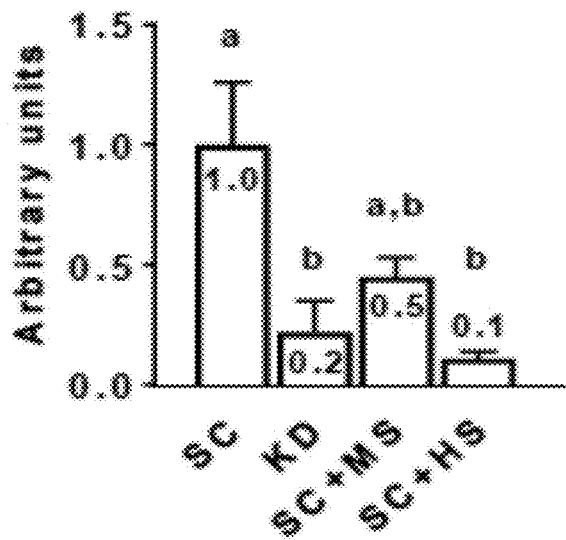
FIG. 10 illustrates a chart illustrating LPL levels in rats following an implementation of an example administration protocol.

A first grouping of 10 rats (labeled SC) were given a standard diet, a second grouping of 10 rats (labeled KD) were given a ketogenic diet, a third grouping of 10 rats (labeled SC+MS) were on the standard diet but given a first dosage of R-beta-hydroxybutyrate salt (e.g., equivalent to 5 g) and a fourth grouping was on the standard iet but given a second dosage of R-beta-hydroxybutyrate salt (e.g., equivalent to 10 g). FIG. 10 illustrates the average Lipoprotien lipase (LPL) in the rats. Since LPL is needed to transport fat into adipose tissue, lowering LPL levels would inhibit fat storage and encourage usage of fat storages. As illustrated, supplementation of a standard diet with even lower dosages of R-beta-hydroxybutyrate decreases LPL levels and thus inhibits fat storage.

Example 11

An individual with high C-reactive protein, which is associated with inflammation, was administered R-beta-hydroxybutyrate. After administration, the C-reactive protein levels were substantially reduced (e.g., 62.5 to 4.4). In addition, fasting glucose was decreased (e.g., 104 to 95).

Example 12

Figure 11:
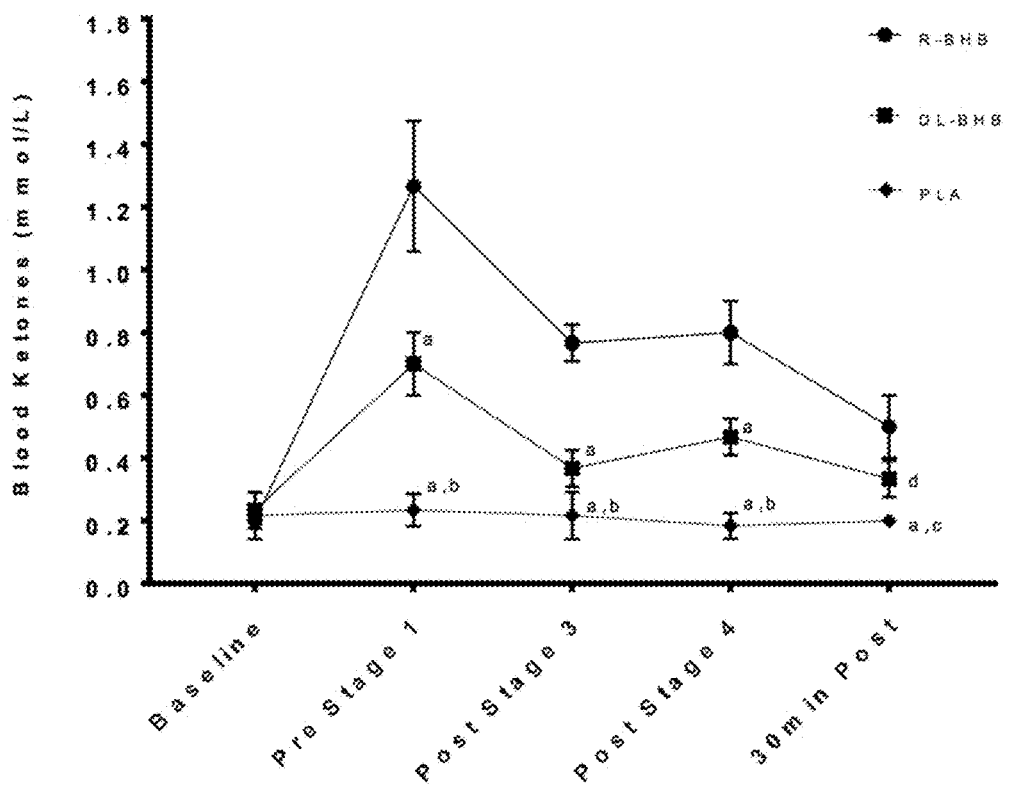
FIG. 11 illustrates a chart illustrating blood ketone levels following an implementation of an example administration protocol.
Figure 12:
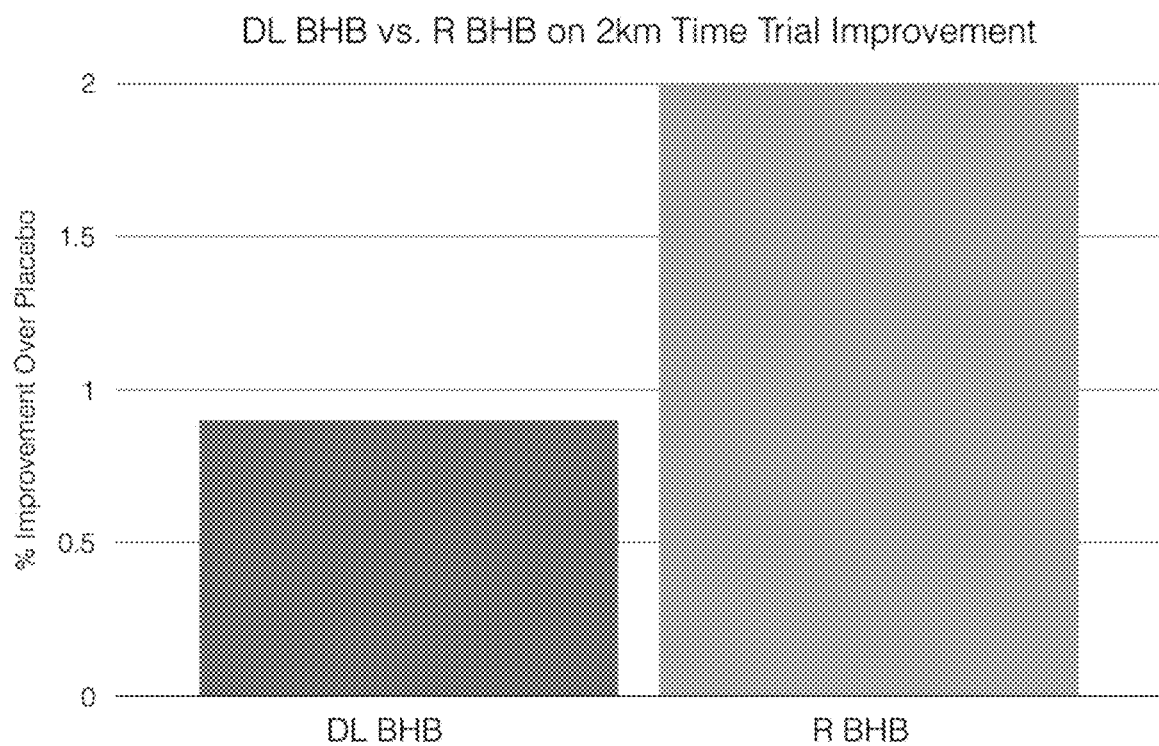
FIG. 12 illustrates a chart illustrating improvement over a placebo following an implementation of an example administration protocol.
Figure 13:
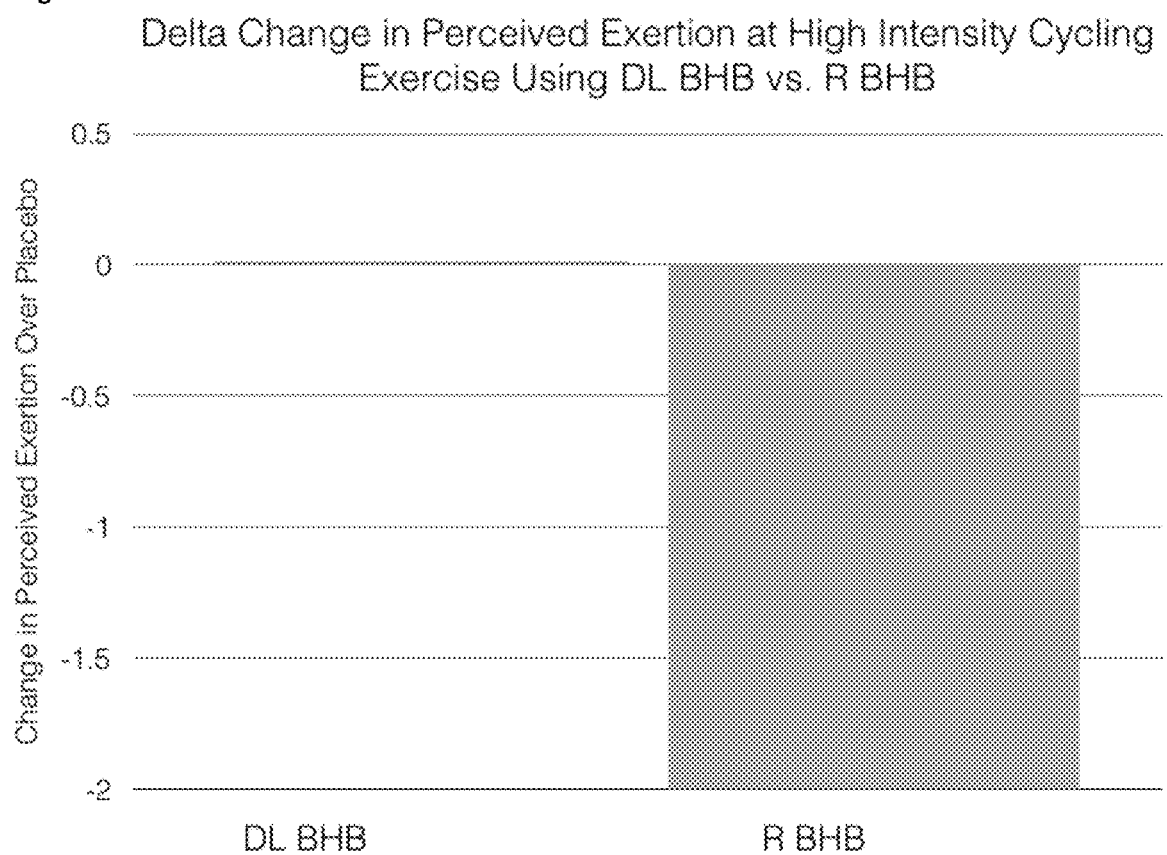
FIG. 13 illustrates a chart illustrating perceived exertion following an implementation of an example administration protocol.

Five healthy individual were given a 2 km time test (e.g., 4 cycles of low to severely intense exercise on a wingate cycle ergometer) 30 minutes after administration of a placebo, 10 g of R-beta-hydroxybutyrate, and 10 g of R-beta-hydroxybutyrate. FIG. 11 illustrates the average blood ketone levels and FIG. 12 illustrates the percentage improvement over the administration of the placebo. As illustrated, blood ketone levels unexpectedly increased more than double during administration of R-beta-hydroxybutyrate when compared with administration of D,L-beta-hydroxybutyrate. In addition, performance (e.g., improvement in time) increased by more than double during administration of R-beta-hydroxybutyrate when compared with D,L-beta-hydroxybutyrate. FIG. 13 illustrates the perceived exertion experienced by the individuals. As illustrated, the individuals did not feel an impact in perceived exertion after administration with D,L-beta-hydroxybutyrate as compared with the perceived exertion improvement experienced after administration of R-beta-hydroxybutyrate. Thus, the R-beta-hydroxybutyrate has an unexpectedly impact on ketone levels and performance.

Example 13

Individuals were given a standard diet or ketogenic diet. Some individuals were administered R-beta-hydroxybutyrate (e.g., 10 g). R-beta-hydroxybutyrate was able to numerically increase superoxide dismutase 2 levels (SOD) in the brain which indicates greater antioxidant capacity in the brain.

Example 14

Figure 14:
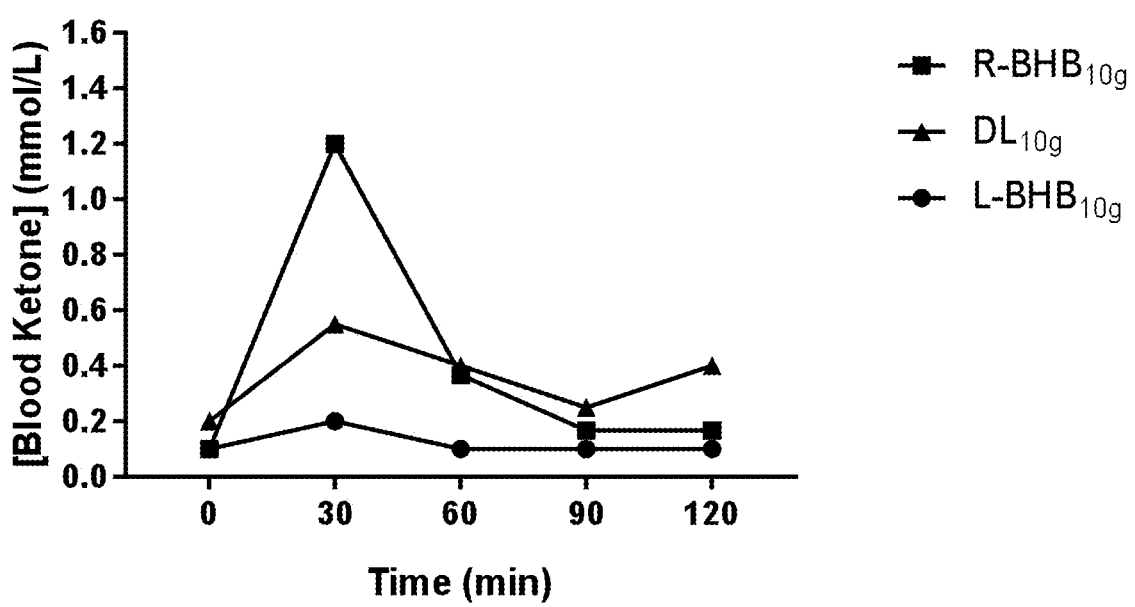
FIG. 14 illustrates a chart illustrating blood ketone levels following an implementation of an example administration protocol.
Figure 15:
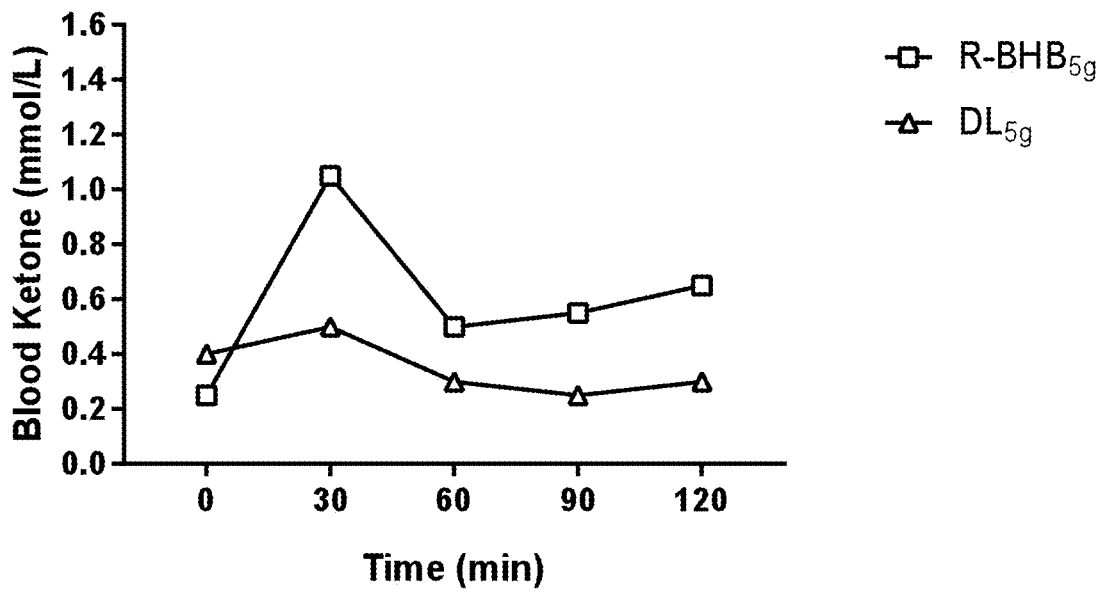
FIG. 15 illustrates a chart illustrating blood ketone levels following an implementation of an example administration protocol.

Individuals were 5 g or 10 mg of R-beta-hydroxybutyrate, L-beta-hydroxybutyrate, or D,L-beta-hydroxybutyrate and blood ketone levels were measured. FIGS. 14 and 15 illustrate the measured blood ketone levels. As illustrated, administration of R-beta-hydroxybutyrate may decrease ketone levels (see e.g., FIGS. 11A and 11B). The reduction of ketone levels occurs even when R-beta-hydroxybutyrate is administered at a dosage of less than 10 g (e.g., approximately 5 g). In addition, unexpectedly (e.g., since it was expected that both the D and L forms of R-beta-hydroxybutyrate behaved in a similar manner), administration of L-beta-hydroxybutyrate does not decrease blood ketones. Furthermore, unexpectedly, even D,L-beta-hydroxybutyrate does not lower blood ketone levels to the same extent as R-beta-hydroxybutyrate. This indicates that L-beta-hydroxybutyrate may block some of the impact of R-beta-hydroxybutyrate, which is unexpected.

Example 15

Figure 16A:
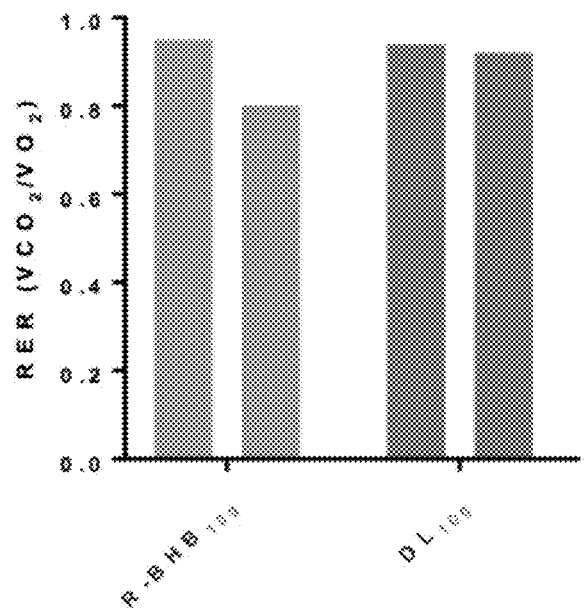
FIG. 16A illustrates a chart illustrating RER levels following an implementation of an example administration protocol.
Figure 16B:
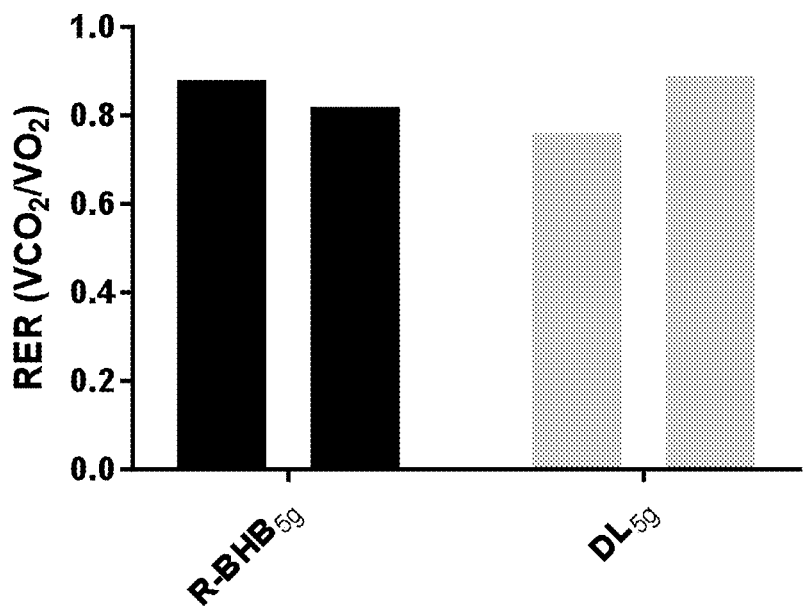
FIG. 16B illustrates a chart illustrating RER levels following an implementation of an example administration protocol.

10 subjects were administered approximately 5 g or 10 g of D,L-beta-hydroxybutyrate or R-beta-hydroxybutyrate, and Respiratory exchange ratio was examined (RER, a ratio of carbon dioxide/oxygen). Generally, a ratio of 1.0 indicates that 100% carbohydrate is used as fuel and at 0.7, 100% fat is used as fuel. As illustrated in FIG. 16A, at 10 g, R-beta-hydroxybutyrate administration reduces RER approximately 3× more than D,L-beta-hydroxybutyrate. As illustrated in FIG. 16B, 5 g of R-beta-hydroxybutyrate is capable of achieving a result that even more D,L-beta-hydroxybutyrate is unable to (e.g., D,L-beta-hydroxybutyrate increases RER by 17% rather than decreasing RER).

Example 16

Figure 17A:
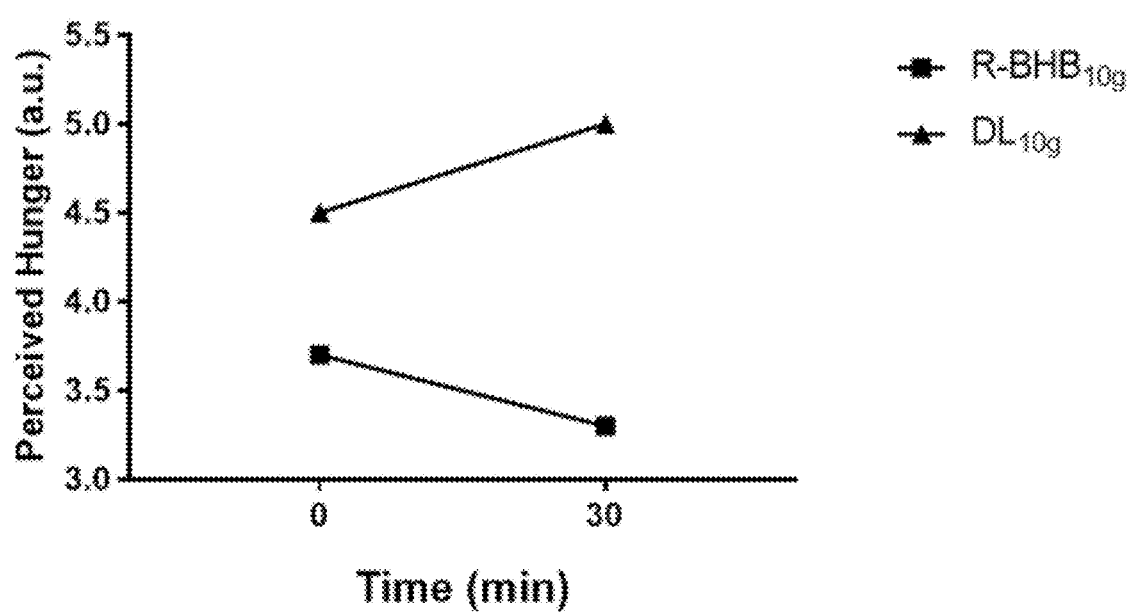
FIG. 17A illustrates a chart illustrating perceived hunger following an implementation of an example administration protocol.
Figure 17B:
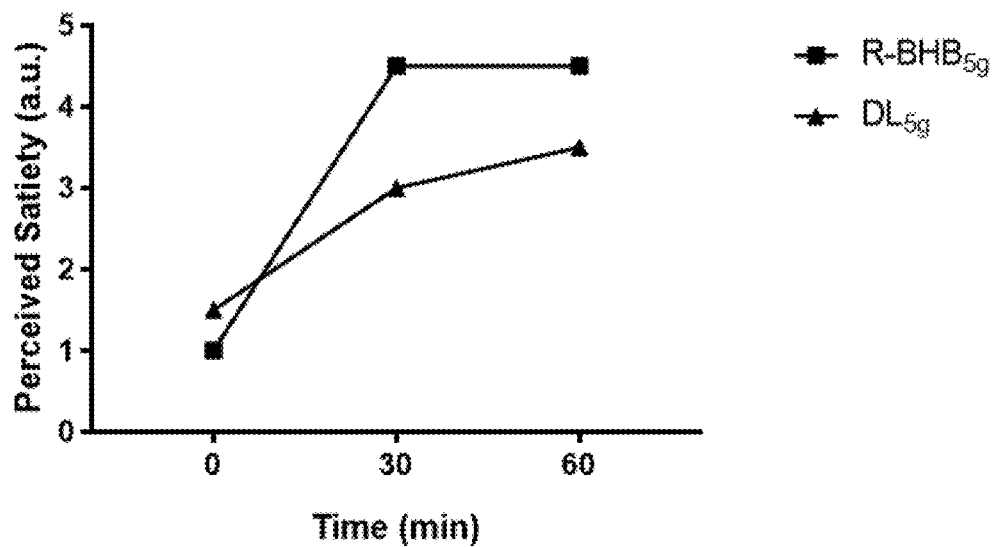
FIG. 17B illustrates a chart illustrating perceived satiety following an implementation of an example administration protocol.
Figure 17C:
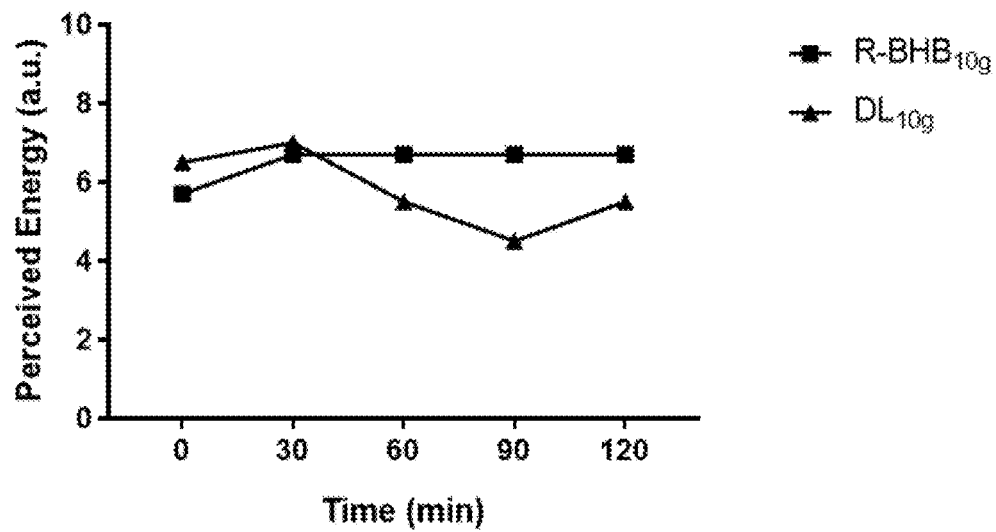
FIG. 17C illustrates a chart illustrating perceived energy following an implementation of an example administration protocol.

Individuals were administered 5 g-10 g of D,L-beta-hydroxybutyrate or R-beta-hydroxybutyrate and tested for perceived hunger, satiety, and perceived energy. FIGS. 13A-13C illustrates the results of the testing. FIG. 17A illustrates perceived hunger, FIG. 17B illustrates perceived satiety, and FIG. 17C illustrates perceived energy. As illustrated in FIG. 17B, at 30 minutes post consumption R-beta-hydroxybutyrate improved satiety levels 2.3× better than DL-beta-hydroxybutyrate relative to baseline levels. As illustrated in FIG. 17C, R-beta-hydroxybutyrate improved perceived energy from 0 to 30 minutes post consumption by double that of D,L-beta-hydroxybutyrate. R-beta-hydroxybutyrate sustained elevated perceived energy levels from 0 minutes at 60, 90, and 120 minutes post consumption, as opposed to D,L-beta-hydroxybutyrate. As illustrated, R-beta-hydroxybutyrate was able to raise perceived energy by 18% and sustain it for 2 hours post ingestion (e.g., more than 2 times greater than the peak value of increase with the DL-beta-hydroxybutyrate)

Example 17

5 young (20s) resistance trained males lifting 50% of their 1-RM on Bench Presses were tested before and after administration of 5 g of R-beta-hydroxybutyrate or D,L-beta-hydroxybutyrate. FIGS. 14A-B illustrate the results of the testing. As illustrated, R-beta-hydroxybutyrate administration resulted in an 11% increase, while DL-beta-hydroxybutyrate administration resulted in only a 2% decrease. Thus, R-beta-hydroxybutyrate experienced a greater than expected impact when compared with D,L-beta-hydroxybutyrate.

The individuals were also tested for power. FIG. 14C illustrates the results of the testing (e.g., averages of power measurements). As illustrated, R-beta-hydroxybutyrate administration increased minimum power by 26%, while the DL-beta-hydroxybutyrate administration raised power by 2%.

Example 18

Individuals were tested for mental acuity before and after administration of 5-10 g of R-beta-hydroxybutyrate or D,L-beta-hydroxybutyrate. Circular Tracking testing (e.g., to assess their cognitive function) was performed and administration of DL-beta-hydroxybutyrate (e.g., 10 g) caused no improvement while the R-beta-hydroxybutyrate (e.g., 10 g) administration caused approximately 3% improvement in tracking accuracy. Vertical Tracking testing (e.g., to assess their cognitive function) was performed and administration of D,L-beta-hydroxybutyrate (e.g., 10 g) improved performance by 4.6%, while the administration of R-beta-hydroxybutyrate (e.g., 10 g) improved performance by 13.8%, which is approximately 3 times greater improvement. Horizontal Saccades testing was performed (e.g., a saccade is one eye movement and known to become significantly slower if cognitive function declines and improve if cognitive function improves). In the horizontal saccades testing, performance improvements were 4 times greater with the administration of R-beta-hydroxybutyrate (e.g., 5 g) than with administration of D,L-beta-hydroxybutyrate (e.g., 13.8% vs. 3.2%). Processing speed testing was performed (e.g., processing speed is considered a true measure of cognitive performance). Administration of R-beta-hydroxybutyrate (e.g., 5 g) improved processing speed by 27.7% and only approximately 18% with administration of the DL-beta-hydroxybutyrate (e.g., 5 g). Response accuracy was also tested. Administration of R-beta-hydroxybutyrate (e.g., 5 g) increased accuracy by 37 percentage points when compared to 12.7% when DL-beta-hydroxybutyrate was administered.

Thus, administration of R-beta-hydroxybutyrate increased mental acuity more than a similar amount of D,L-beta-hydroxybutyrate. In fact, as the testing revealed, the administration of R-beta-hydroxybutyrate increased mental acuity often by than double when compared with a similar amount of D,L-beta-hydroxybutyrate.

Example 19

Figure 19:
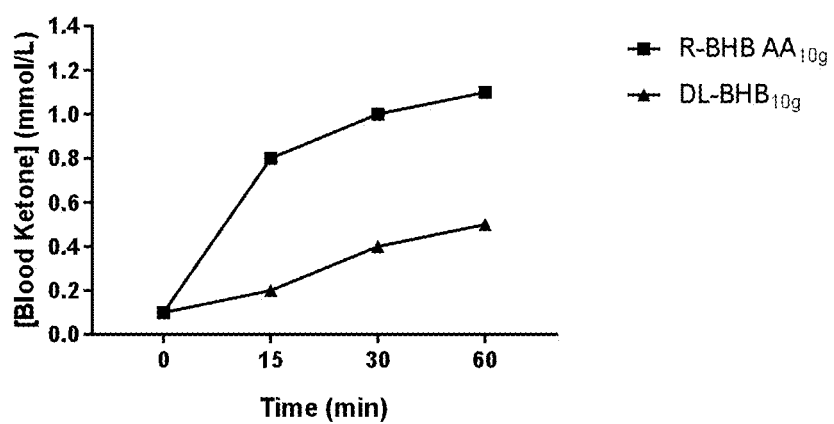
FIG. 19 illustrates a chart illustrating blood ketone levels following an implementation of an example administration protocol.

The compound for administration was prepared to include an R-beta-hydroxybutyrate amino acid complex. An R-beta-hydroxybutyrate Agmatine complex was prepared and an R-beta-hydroxybutyrate Arginine complex was prepared. FIG. 19 illustrates the average blood ketone levels achieved with the R-beta-hydroxybutyrate amino acid complex (e.g., an average of both complexes) when compared with D,L-beta-hydroxybutyrate. As illustrated, blood ketone levels are not only more than double the blood ketone levels achieved with the same quantity of D,L-beta-hydroxybutyrate as R-beta-hydroxybutyrate amino acid complex (e.g., 10 g), but they are more than an additive result of a similar amount of R-beta-hydroxybutyrate and amino acid.

Use of the R-beta-hydroxybutyrate amino acid complex may reduce the amount of cation delivered (e.g. since the complex may deliver the R-beta-hydroxybutyrate rather than a R-beta-hydroxybutyrate salt). The reduction of this cation may decrease side effects (e.g., from increased sodium, potassium, and/or magnesium intake), increase user satisfaction, and/or increase the population that can tolerate the administration of R-beta-hydroxybutyrate (e.g., since some individuals may not be capable of increasing loads of these cations due to underlying diseases and/or disorder). The use of the R-beta-hydroxybutyrate amino acid complex may also allow a higher yield of R-beta-hydroxybutyrate to be administered (90.8% R-beta-hydroxybutyrate, 5% amino acid) when compared with a similar weight of R-beta-hydroxybutyrate salt (e.g., average of 83% yield for BHB sodium).

Example 20

Figure 20:
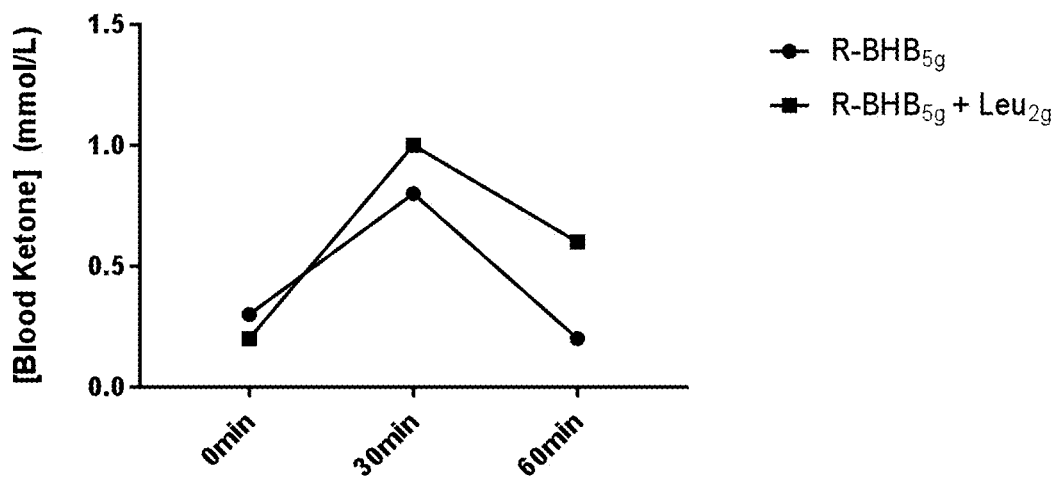
FIG. 20 illustrates a chart illustrating blood ketone levels following an implementation of an example administration protocol.

A composition for administration may include R-beta-hydroxybutyrate and an amino acid, such as Leucine. The R-beta-hydroxybutyrate and leucine maybe complexed and/or mixed together for administration. The R-beta-hydroxybutyrate and leucine may be administered separately but approximately concurrently. FIG. 20 illustrates the blood ketone levels after administration of R-beta-hydroxybutyrate (5 g) and leucine (2 g). As illustrated, the administration of R-beta-hydroxybutyrate and leucine causes greater elevation of blood ketone levels than the administration of R-beta-hydroxybutyrate (5 g). The administration of R-beta-hydroxybutyrate and leucine causes greater elevation of blood ketone levels than merely the additive effect of similar quantities of R-beta-hydroxybutyrate and leucine administered separately.

END OF EXAMPLES

In various implementations, a pharmaceutically effective amount of butyrate, beta-hydroxybutyrate, related compounds, and/or one or more other compounds may be administered to an individual. For example, the pharmaceutically effective amount of the beta-hydroxybutyrate, related compounds, and/or one or more other compounds may be administered to cause weight loss, weight maintenance, elevate blood ketone levels, maintain blood ketone levels, reduce blood glucose levels, maintain blood glucose levels, improve focus, energy, cognitive function, traumatic brain injury, diabetes, neurological disorders, cancer, inflammatory conditions, suppressing appetite, anti-aging, anti-glycation, epilepsy, depression, performance, strength, muscle mass, fat loss, body composition, and/or use as a medicament etc. The pharmaceutically effective amount of butyrate, beta-hydroxybutyrate, related compounds, and/or combinations thereof may be administered to healthy individuals and/or not healthy individuals (e.g., with diseases and/or disorders).

Implementations may include one or more of the following features. The beta-hydroxybutyrate may include the racemic mixture and/or the individual isomers of beta-hydroxybutyrate, such as R-beta-hydroxybutyrate (also known as D-beta-hydroxybutyrate). The beta-hydroxybutyrate may include related compounds. The beta-hydroxybutyrate may be coupled to a compound such as an amino acid. The beta-hydroxybutyrate may include beta-hydroxybutyrate salt and beta-hydroxybutyrate esters, in some implementations. Other compounds may include short chain fatty acids, short chain triglycerides, medium chain fatty acids, medium chain triglycerides, long chain fatty acids, long chain triglycerides, berberine, berberine metabolites, dihydroberberine, tetrahydroberberine and/or combinations thereof. One or more of the other compounds may be unencapsulated and/or encapsulated.

In various implementations, a composition may be administered to induce and/or maintain ketosis. The composition may include approximately 0.5 g to approximately 10 g of R-beta-hydroxybutyrate.

Implementations may include one or more of the following features. The amount of the composition administered may include approximately 0.5 to approximately 3 g of R-beta-hydroxybutyrate. The composition may include additional composition, such as compositions that are capable of independently increasing ketone levels, inducing ketosis, and/or maintaining ketosis. In some implementations, the composition may include additional compositions to provide other health benefits (e.g., increase mental acuity, strength, etc.). For example, the composition may include fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. The composition may include flavoring(s), vitamin(s), mineral(s), and/or binder(s). The composition may be administered up to 5 times daily. The administration of the composition may increase strength, mental acuity, metabolism, fat loss, fat oxidation, motor function, muscle mass, and/or combinations thereof. In some implementations, the 0.5 to 10 g of R-beta-hydroxybutyrate administered includes R-beta-hydroxybutyrate and at least one of a polymer of R-beta-hydroxybutyrate or R-beta-hydroxybutyrate-complex.

In various implementations, a composition may include approximately 0.5 g to approximately 10 g of R-beta-hydroxybutyrate and one or more additional compounds capable of maintaining ketosis independently. Administration of the composition may induce and/or maintains ketosis in an individual.

Implementations may include one or more of the following features. The R-beta-hydroxybutyrate may include R-beta-hydroxybutyrate salt, R-beta-hydroxybutyrate-amino acid complex, and/or R-beta-hydroxybutyrate polymer. The additional compounds may include fatty acids and/or esters of fatty acids. The fatty acids and/or esters may include natural (e.g., cream, coconut oil, macadamia oil, etc.) and/or artificial fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. In some implementations, additional compound(s) may include polymer(s) of beta-hydroxybutyrate, D,L-beta-hydroxybutyrate, butyrate, butyric acid, and/or triglyceride tributyrin. The additional compound(s) may include berberine, dihydroberberine, and/or tetrahydroberberine.

In various implementations, pharmaceutically effective amounts of R-beta-hydroxybutyrate and amino acid may be administered for inducing and/or maintaining ketosis.

Implementations may include one or more of the following features. The amount of R-beta-hydroxybutyrate to induce and/or maintain ketosis in an individual may be less than or equal to half of the amount of D,L-beta-hydroxybutyrate to induce and/or maintain the same level of ketosis (e.g., as measured by blood ketone levels). In some implementations, the amount of R-beta-hydroxybutyrate to induce and/or maintain ketosis in an individual may be less than the amount of D,L-beta-hydroxybutyrate or L-beta-hydroxybutyrate to induce and/or maintain the same level of ketosis. The composition may include approximately 1 g to approximately 5 grams of R-beta-hydroxybutyrate and approximately 0.5 to 2 g of amino acid. The amino acid may include Leucine. The composition may include a mixture and/or complex of the R-beta-hydroxybutyrate and amino acid. At least a portion of the R-beta-hydroxybutyrate may be complexed with the amino acid, in some implementations. For example, a portion of the R-beta-hydroxybutyrate may be administered in the composition as a salt and/or polymer and another portion of the R-beta-hydroxybutyrate may be administered as a complex with an amino acid (e.g., leucine). In some implementations, the composition may include at least one R-beta-hydroxybutyrate salt (e.g., in additional to the pharmaceutically effective amounts of R-beta-hydroxybutyrate in the composition and/or as the pharmaceutically effective amounts of R-beta-hydroxybutyrate).

In various implementations, beta-hydroxybutyrate may administered simultaneously and/or sequentially with one or more other compounds (e.g., short chain, medium chain, and/or long chain fatty acids). For example, beta-hydroxybutyrate and/or one or more other compounds may be delivered mixed in a powdered, liquid, gel, and/or other appropriate form. In some implementations, the beta-hydroxybutyrate and/or one or more other compounds may be administered via pills, tablets, capsules, other oral administration forms, intravenously, nasal sprays, sublingual tabs/strips, or topical delivery, rectal, other appropriate administration forms, and/or combinations thereof.

The described compositions may be administered via any appropriate administration method. For example, the described compositions may be administered enterally and/or parenterally. In some implementations, the described composition may be administered via a tablet and/or capsule. In some implementations, the described composition may be administered via tablet, capsule, powdered supplement; ready-to-drink formulation; topical product including transdermals; cosmeceutical product; foods such bars, cookies, gum, candy, functional foods; toothpaste, sublingual product; injection; intravenous fluids; beverages such as shots or energy shots; inhalers; sublinguals; and/or combinations thereof. The described composition may be provided in a powdered form that allows the described composition to be sprinkled on food, mixed with a liquid to provide a beverage, directly administered.

The described compositions may be administered on an administration protocol to improve glucose tolerance (e.g., fasting glucose levels may be reduced and/or glucose metabolism may be improved), in some implementations. The described compositions may be administered on an administration protocol to increase ketone levels (e.g., blood and/or urine ketone concentrations). For example, the described compositions may be administered once a day, via a time released or extended release preparation, and/or multiple times a day. The described composition may replace other pharmaceuticals taken for improving glucose tolerance, such as metformin, and/or be utilized in combination with one or more other pharmaceuticals, as appropriate.

In some implementations, an administration schedule may include administration of different berberine metabolite compositions at different periods. For example, berberine metabolite compositions may include at least a first composition and a second composition. The first composition may include dihydroberberine. The second composition may include dihydroberberine and a first additional compound that is capable of independently increasing blood ketone levels. The first composition may be administered to an individual for a first period of time and the second composition may be administered to the same individual for a second period of time. In some implementations, a third composition comprising dihydroberberine and a second additional compound that is different from the first additional compound may be administered. The first and other compositions (e.g., second and/or third composition) may be administered alternatively, sequentially, and/or in conjunction with each other (e.g., with a second and/or third composition). The compound formulations (e.g., dihydroberberine and/or which additional compounds are included) may be selected based on user preference (e.g., taste, diseases, sensitivities), desired results (e.g., fast induction of ketosis and/or maintenance), etc.

In various implementations, although a berberine metabolite such as dihydroberberine and/or tetrahydroberberine may be described, other forms of dihydroberberine and/or tetrahydroberberine may be administered such as salts, complexes, and/or derivatives thereof.

Although various described systems and processes have been described as a being administered in humans, the described systems and processes may be administered to other mammals, such as rats, dogs, etc.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a beta-hydroxybutyrate" includes a combination of two or more beta-hydroxybutyrates and reference to "an additive" includes different types and/or combinations of additives.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method of managing glucose tolerance in an individual, the method comprising:
    administering, to an individual a pharmaceutically effective amount of a composition, the composition comprising:
        approximately 25 mg to approximately 800 mg of dihydroberberine; and
        less than approximately 10 mg of R-beta-hydroxybutyrate,
        wherein the composition comprises pure R-beta-hydroxybutyrate or a non-racemic mixture of R-beta-hydroxybutyrate and L-beta-hydroxybutyrate.

2. The method of claim 1, wherein the administration of the composition results in at least one of reduced fasting glucose level or maintained ketosis in the individual.

3. The method of claim 1, wherein the dihydroberberine is administered as a complexed composition, and wherein the complexed composition further comprises at least one of complexed phytosomes or liposomes.

4. The method of claim 1, wherein the dihydroberberine is provided as a microemulsion including dihydroberberine.

5. The method of claim 1, wherein the composition is administered at least once daily.

6. The method of claim 1, wherein the composition further comprises a Cytochrome P450 inhibitor, wherein administration of the Cyctochrome P450 inhibitor allows for a decrease of the amount of the composition administered to be sufficient to achieve the desired results.

7. The method of claim 1, wherein the non-racemic mixture comprises greater than 90 percent of R-beta-hydroxybutyrate and less than 10% of L-beta-hydroxybutyrate.

8. The method of claim 1, wherein the R-beta-hydroxybutyrate comprises at least one of a salt of R-beta-hydroxybutyrate or a polymer of R-beta-hydroxybutyrate.

9. The method of claim 1, wherein the composition further comprises a fatty acid or an ester thereof, and wherein the fatty acid comprises at least one of a medium chain fatty acid, a short chain fatty acid, or a long chain fatty acid.

10. The method of claim 9, wherein the fatty acid or ester thereof comprises at least one of coconut oil, coconut butter, or coconut milk.

11. A method of managing glucose tolerance in an individual, the method comprising:
    administering, to an individual a pharmaceutically effective amount of a composition, the composition comprising:

approximately 25 mg to approximately 800 mg of dihydroberberine; and less than approximately 10 g of R-beta-hydroxybutyrate.

12. The method of claim 11, wherein the administration of composition maintains ketosis in the individual.

13. The method of claim 11, wherein the composition comprises pure R-beta-hydroxybutyrate or a non-racemic mixture that comprises at least 90 percent R-beta-hydroxybutyrate and less than 10 percent L-beta-hydroxybutyrate.

14. The method of claim 11, wherein the R-beta-hydroxybutyrate comprises at least one of a salt of R-beta-hydroxybutyrate or a polymer of R-beta-hydroxybutyrate.

15. The method of claim 11, the composition further comprising at least one of a fatty acid or ester of a fatty acid.

16. The method of claim 1, wherein the composition comprises pure R-beta-hydroxybutyrate.

17. The method of claim 11, wherein the dihydroberberine is administered as a complexed composition, and wherein the complexed composition further comprises at least one of complexed phytosomes or liposomes.

18. The method of claim 11, wherein the dihydroberberine is provided as a microemulsion including dihydroberberine.

19. The method of claim 11, wherein the composition is administered at least once daily.

20. The method of claim 11, wherein the composition further comprises a Cytochrome P450 inhibitor, wherein administration of the Cyctochrome P450 inhibitor allows for a decrease of the amount of the composition administered to be sufficient to achieve the desired results.

* * * * *